US012622791B2

(12) United States Patent
Rama et al.

(10) Patent No.: US 12,622,791 B2
(45) Date of Patent: May 12, 2026

(54) DEVICES AND SYSTEMS FOR ASSESSING LAXITY IN A JOINT

(71) Applicants: Smith & Nephew, Inc., Memphis, TN (US); Smith & Nephew Asia Pacific PTE. Limited, Singapore (SG); Smith & Nephew Orthopaedics AG, Zug (CH)

(72) Inventors: Suraj Rama, Pittsburgh, PA (US); James Kromka, Monroeville, PA (US); Samuel C. Dumpe, Sewickley, PA (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 274 days.

(21) Appl. No.: 18/613,461

(22) Filed: Mar. 22, 2024

(65) Prior Publication Data

US 2024/0315906 A1     Sep. 26, 2024

Related U.S. Application Data

(60) Provisional application No. 63/454,381, filed on Mar. 24, 2023.

(51) Int. Cl.
    *A61F 2/46*      (2006.01)
    *A61B 17/17*     (2006.01)
    *A61G 13/12*     (2006.01)

(52) U.S. Cl.
    CPC .......... *A61F 2/468* (2013.01); *A61G 13/1245* (2013.01); *A61G 13/1255* (2013.01); *A61G 13/129* (2013.01)

(58) Field of Classification Search
    CPC ........ A61G 13/129; A61B 17/17; A61F 2/468
    See application file for complete search history.

(56) References Cited

U.S. PATENT DOCUMENTS

2013/0096563 A1*  4/2013  Meade ................. A61B 17/154
                                                     606/88
2019/0046217 A1*  2/2019  Rasmussen .......... A61B 17/025
                          (Continued)

FOREIGN PATENT DOCUMENTS

WO         2021222216 A1    11/2021

OTHER PUBLICATIONS

European Patent Office, European Search Report, dated Aug. 8, 2024, 11 pages.

*Primary Examiner* — Christian A Sevilla
(74) *Attorney, Agent, or Firm* — KDW Firm PLLC

(57) ABSTRACT

A device for assessing laxity of a joint is disclosed. The device comprises a trial component comprising a base plate configured to couple to a tibia of the joint and a superior spacer coupled to the base plate. The base plate and the superior spacer define a cavity therebetween that may receive a portion of a tensioner tool. When force is applied via the tensioner tool, the superior spacer is configured to be selectively moved from a first position in contact with a superior surface of the base plate to a second position separated from the superior surface. A system for assessing laxity of a joint including a first bone and a second bone is also disclosed. The system comprises the trial component, the tensioner tool, and a processor configured to determine a gap distance associated with the first bone and the second bone during tensioning.

22 Claims, 15 Drawing Sheets

(56)     References Cited

U.S. PATENT DOCUMENTS

| 2021/0015693 A1* | 1/2021 | Lim | .................. | A61G 13/1255 |
| 2022/0361895 A1* | 11/2022 | Rasmussen | ........ | A61B 17/1659 |
| 2022/0362036 A1* | 11/2022 | Rasmussen | ........ | A61B 17/1764 |

* cited by examiner

400

410

405

405B

405A

430

700

TENSIONER TOOL

705

TRIAL COMPONENT

710

TRACKING DEVICE

720

CONTROL UNIT

715

PROCESSOR    MEMORY

800

Apply Trial Component to Tibia

805

Insert Tensioner Tool to Cavity of Trial Component

810

Separate Arms of Tensioner Tool to Lift Spacer

815

Determine Distance of Spacer from Base in Lifted Position

820

1000

DEVICES AND SYSTEMS FOR ASSESSING LAXITY IN A JOINT

CROSS-REFERENCE TO RELATED APPLICATIONS

This application claims the benefit of priority to U.S. Provisional Application No. 63/454,381 entitled "Devices and Systems for Assessing Laxity in a Joint," filed Mar. 24, 2023, which is incorporated herein by reference in its entirety.

TECHNICAL FIELD

The present disclosure relates generally to methods, systems, and apparatuses related to assessing laxity of a joint. More particularly, the present disclosure relates to assessing laxity of a joint using a trial component and a tensioner tool. The disclosed techniques may be applied to, for example, knee arthroplasties, but may also apply to shoulder arthroplasties, hip arthroplasties, and other surgical interventions.

BACKGROUND

In joint arthroplasties such as total knee arthroplasty (TKA), tensioning the collateral ligaments provides objective system inputs to help aid in implant planning. While various devices are available for tensioning joints, the available tools rely on prior bony resection.

Furthermore, tools that may enable tensioning with limited resection still suffer from the limitation of a minimum gap. For example, FIG. 10 depicts a tensioner tool inserted in a knee joint in accordance with an embodiment. As shown, the tensioner tool 1000 may have an insertion tip for a profile configured for insertion in a limited space between the femur and the tibia of a knee joint. The insertion tip may be inserted in a medial compartment, a lateral compartment, adjacent the medial condyle of the femur, adjacent the lateral condyle of the femur, centrally between the condyles, and/or at additional positions with respect to features of the femur and tibia. When inserted, a force may be applied to a handle of the tensioner tool 1000 to cause a distraction force at a contact surface upon the bones, i.e., a surface of the insertion tip in contact with the bones. The applied force may be sensed and registered by force sensors on the tensioner tool, e.g., a strain gauge or another force sensor as would be known to a person having an ordinary level of skill in the art. Further, the distraction force may cause the femur and the tibia to separate, resulting in pivoting of the arms of the tensioner tool and formation of a gap between the femur and the tibia. The applied force and/or the gap distance may be recorded to perform calculations related to the biomechanics of the knee joint.

However, as shown in FIG. 10, insertion of the tensioner tool 1000 between the femur and the tibia creates a minimum gap profile therebetween due to the thickness of the tensioner tool 1000. Accordingly, while a surgeon may prefer a surgical plan including a gap profile less than the thickness of the insertion tip of the tensioner tool, it may not be possible to verify the gap profile for a set force target using a tensioner tool 1000, thereby limiting the assessment of useful post-operative joint laxity measurements.

As such, it would be advantageous to have a system for measuring and assessing a joint laxity that facilitates a gap profile less than a thickness of the tensioner tool, thereby enabling surgeons to measure a lower minimum gap during post-operative trialing.

SUMMARY

A device for assessing laxity in a joint is provided. The device comprises a trial component configured to be coupled to a first bone of the joint, the trial component comprising a base plate configured to couple to the first bone and a superior spacer coupled to the base plate, wherein the base plate and the superior spacer define a cavity therebetween, the cavity configured to receive a portion of a tensioner tool, wherein the superior spacer is configured to be selectively moved between a first position in contact with a superior surface of the base plate and a second position separated from the superior surface.

According to some embodiments, the superior surface comprises a keying feature configured to mate with a surface feature on the portion of the tensioner tool, thereby securing an anterior-posterior pose of the tensioner tool.

According to some embodiments, a cross-sectional geometry of the superior surface substantially matches a cross-sectional geometry of the superior spacer.

According to some embodiments, the superior spacer pivots with respect to the superior surface of the base plate as the superior spacer moves between the first position and the second position.

According to some embodiments, the superior spacer translates along a longitudinal axis of the base plate as the superior spacer moves between the first position and the second position. According to additional embodiments, translation of the superior spacer is locked with respect to a first axis and a second axis, wherein the first axis is orthogonal to the second axis, wherein each of the first axis and the second axis is orthogonal to the longitudinal axis.

According to some embodiments, the superior spacer is formed from a polymer.

According to some embodiments, the joint is a knee joint and the first bone is a tibia.

According to some embodiments, the joint is a shoulder joint.

A system for assessing laxity in a joint is also provided. The joint has a first bone and a second bone. The system comprises a tensioner tool comprising a pair of arms defining an insertion portion, wherein the pair of arms are configured to pivot about a pivot axis between a compressed configuration and an expanded configuration; a trial component comprising: a base plate configured to couple to the first bone, and a superior spacer coupled to the base plate, wherein the superior spacer is configured to be selectively moved between a first position in contact with a superior surface of the base plate and a second position separated from the superior surface, wherein the base plate and the superior spacer define a cavity therebetween, the cavity configured to receive the insertion portion of the tensioner tool therein; a processor; and a non-transitory, computer-readable medium storing instructions that, when executed, cause the processor to: receive information related to a distance between the superior surface of the base plate and the superior spacer in the second position, and determine, based on the information, a gap distance associated with the first bone and the second bone.

According to some embodiments, the cavity is configured to receive the insertion portion of the tensioner tool in the compressed configuration.

According to some embodiments, the superior spacer is configured to move from the first position to the second position when the tensioner tool pivots from the compressed configuration to the expanded configuration within the cavity.

According to some embodiments, the superior surface comprises a first keying feature and tensioner tool comprises a second keying feature complementary to the first keying feature, wherein the first keying feature is configured to mate with the second keying feature when the insertion portion is received within the cavity.

According to some embodiments, the first keying feature, when mated with the second keying feature, secures an anterior-posterior pose of the tensioner tool.

According to some embodiments, a cross-sectional geometry of the superior surface substantially matches a cross-sectional geometry of the superior spacer.

According to some embodiments, the superior spacer pivots with respect to the superior surface of the base plate as the superior spacer moves between the first position and the second position.

According to some embodiments, the superior spacer translates along a longitudinal axis of the base plate as the superior spacer moves between the first position and the second position. According to additional embodiments, translation of the superior spacer is locked with respect to a first axis and a second axis, wherein the first axis is orthogonal to the second axis, wherein each of the first axis and the second axis is orthogonal to the longitudinal axis.

According to some embodiments, the superior spacer is formed from a polymer.

According to some embodiments, the joint is a knee joint, the first bone is a tibia, and the second bone is a femur.

According to some embodiments, the joint is a shoulder joint.

A method of assessing laxity in a joint is also provided. The method comprises applying trial component to a first bone of the joint, the trial component comprising a base plate configured to couple to the first bone and a superior spacer coupled to the base plate; inserting an insertion portion of a tensioner tool within a cavity defined between the base plate and the superior spacer, the insertion portion comprising a pair of arms; separating the pair of arms, thereby causing the superior spacer to move from a first position in contact with a superior surface of the base plate to a second position spaced from the superior surface; and determining a first distance between the superior surface of the base plate and the superior spacer in the second position.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings.

DETAILED DESCRIPTION

Figure 1:
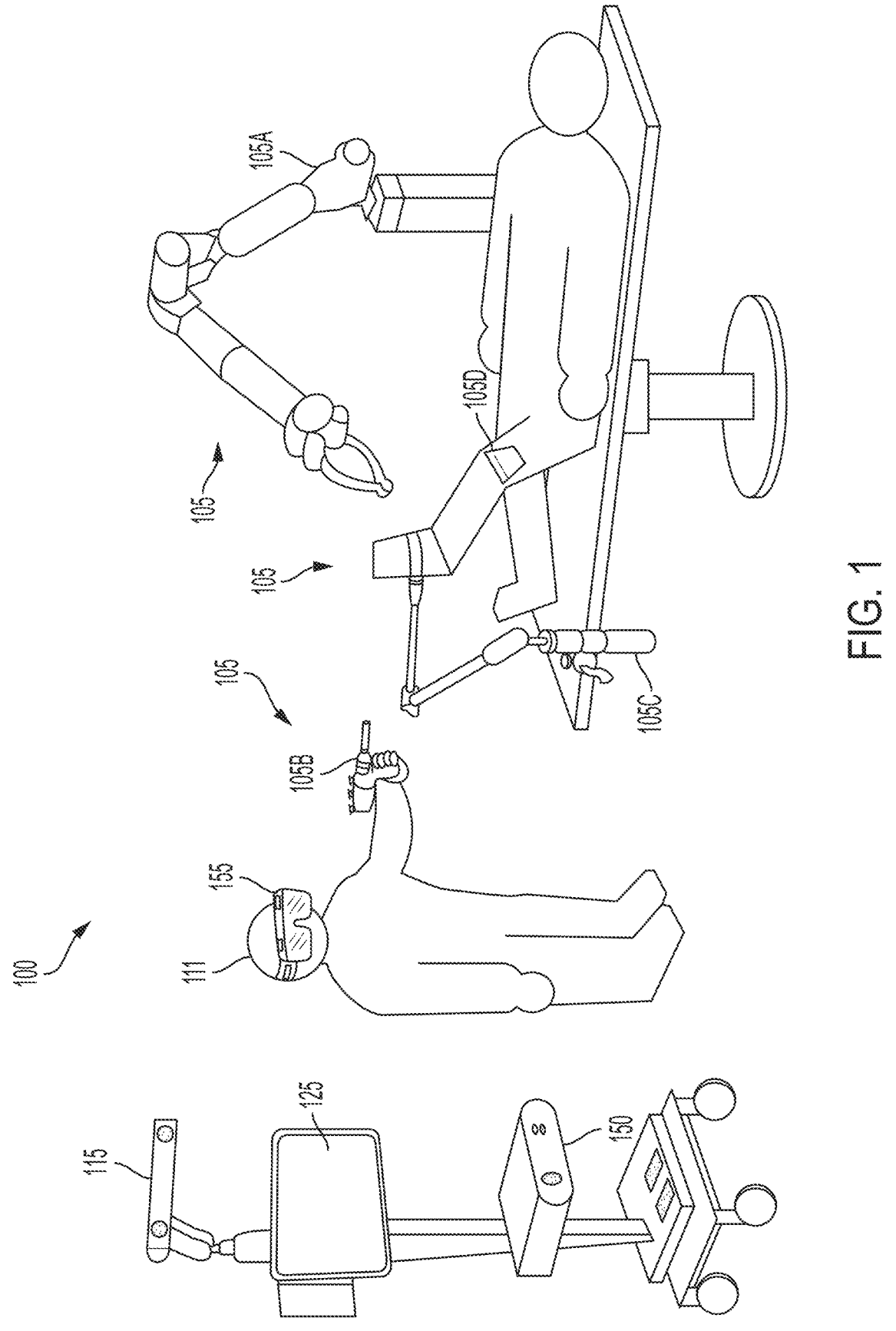
FIG. 1 depicts an operating theatre including an illustrative computer-assisted surgical system (CASS) in accordance with an embodiment.

This disclosure is not limited to the particular systems, devices and methods described, as these may vary. The terminology used in the description is for the purpose of describing the particular versions or embodiments only and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Definitions

For the purposes of this disclosure, the term "implant" is used to refer to a prosthetic device or structure manufactured to replace or enhance a biological structure. For example, in a total hip replacement procedure a prosthetic acetabular cup (implant) is used to replace or enhance a patients worn or damaged acetabulum. While the term "implant" is generally considered to denote a man-made structure (as contrasted with a transplant), for the purposes of this specification an implant can include a biological tissue or material transplanted to replace or enhance a biological structure.

For the purposes of this disclosure, the term "real-time" is used to refer to calculations or operations performed on-the-fly as events occur or input is received by the operable system. However, the use of the term "real-time" is not intended to preclude operations that cause some latency between input and response, so long as the latency is an unintended consequence induced by the performance characteristics of the machine.

For the purposes of this disclosure, the terms "distract," "distracting," or "distraction" are used to refer to displacement of a first point with respect to a second point. For example, the first point and the second point may correspond to surfaces of a joint. In some embodiments herein, a joint may be distracted, i.e., portions of the joint may be separated and/or moved with respect to one another to place the joint under tension. In some embodiments, a first portion of the joint be a surface of a femur and a second portion of the joint may be a surface of a tibia such that separation occurs between the bones of the joint. In additional embodiments, a first portion of the joint may be a first portion of a tibial implant component or a tibial trial implant and a second portion of the joint may be a second portion of the tibial implant component or the tibial trial implant that is movable with respect to the first portion (e.g., a base plate and a superior spacer as described herein). Accordingly, separation may occur between the portions of the tibial implant component or the tibial trial implant (i.e., intra-implant separation). Throughout the disclosure herein, the described embodiments may be collectively referred to as distraction of the joint.

Although much of this disclosure refers to surgeons or other medical professionals by specific job title or role, nothing in this disclosure is intended to be limited to a specific job title or function. Surgeons or medical professionals can include any doctor, nurse, medical professional, or technician. Any of these terms or job titles can be used interchangeably with the user of the systems disclosed herein unless otherwise explicitly demarcated. For example, a reference to a surgeon also could apply, in some embodiments to a technician or nurse.

The systems, methods, and devices disclosed herein are particularly well adapted for surgical procedures that utilize surgical navigation systems, such as the NAVIO® surgical navigation system. CORI is a registered trademark of BLUE BELT TECHNOLOGIES, INC. of Pittsburgh, PA, which is a subsidiary of SMITH & NEPHEW, INC. of Memphis, TN.

CASS Ecosystem Overview

FIG. 1 provides an illustration of an example computer-assisted surgical system (CASS) 100, according to some embodiments. As described in further detail in the sections that follow, the CASS uses computers, robotics, and imaging technology to aid surgeons in performing orthopedic surgery procedures such as total knee arthroplasty (TKA) or THA. For example, surgical navigation systems can aid surgeons in locating patient anatomical structures, guiding surgical instruments, and implanting medical devices with a high degree of accuracy. Surgical navigation systems such as the CASS 100 often employ various forms of computing technology to perform a wide variety of standard and minimally invasive surgical procedures and techniques. Moreover, these systems allow surgeons to more accurately plan, track and navigate the placement of instruments and implants relative to the body of a patient, as well as conduct pre-operative and intra-operative body imaging.

An Effector Platform 105 positions surgical tools relative to a patient during surgery. The exact components of the Effector Platform 105 will vary, depending on the embodiment employed. For example, for a knee surgery, the Effector Platform 105 may include an End Effector 105B that holds surgical tools or instruments during their use. The End Effector 105B may be a handheld device or instrument used by the surgeon (e.g., a CORI® hand piece or a cutting guide or jig) or, alternatively, the End Effector 105B can include a device or instrument held or positioned by a robotic arm 105A. While one robotic arm 105A is illustrated in FIG. 1, in some embodiments there may be multiple devices. As examples, there may be one robotic arm 105A on each side of an operating table T or two devices on one side of the table T. The robotic arm 105A may be mounted directly to the table T, be located next to the table T on a floor platform (not shown), mounted on a floor-to-ceiling pole, or mounted on a wall or ceiling of an operating room. The floor platform may be fixed or moveable. In one particular embodiment, the robotic arm 105A is mounted on a floor-to-ceiling pole located between the patient's legs or feet. In some embodiments, the End Effector 105B may include a suture holder or a stapler to assist in closing wounds. Further, in the case of two robotic arms 105A, the surgical computer 150 can drive the robotic arms 105A to work together to suture the wound at closure. Alternatively, the surgical computer 150 can drive one or more robotic arms 105A to staple the wound at closure.

The Effector Platform 105 can include a Limb Positioner 105C for positioning the patient's limbs during surgery. One example of a Limb Positioner 105C is the SMITH AND NEPHEW SPIDER2 system. The Limb Positioner 105C may be operated manually by the surgeon or alternatively change limb positions based on instructions received from the Surgical Computer 150 (described below). While one Limb Positioner 105C is illustrated in FIG. 1, in some embodiments there may be multiple devices. As examples, there may be one Limb Positioner 105C on each side of the operating table T or two devices on one side of the table T. The Limb Positioner 105C may be mounted directly to the table T, be located next to the table T on a floor platform (not shown), mounted on a pole, or mounted on a wall or ceiling of an operating room. In some embodiments, the Limb Positioner 105C can be used in non-conventional ways, such as a retractor or specific bone holder. The Limb Positioner 105C may include, as examples, an ankle boot, a soft tissue clamp, a bone clamp, or a soft-tissue retractor spoon, such as a hooked, curved, or angled blade. In some embodiments, the Limb Positioner 105C may include a suture holder to assist in closing wounds.

The Effector Platform 105 may include tools, such as a screwdriver, light or laser, to indicate an axis or plane, bubble level, pin driver, pin puller, plane checker, pointer, finger, or some combination thereof.

Resection Equipment 110 (not shown in FIG. 1) performs bone or tissue resection using, for example, mechanical, ultrasonic, or laser techniques. Examples of Resection Equipment 110 include drilling devices, burring devices, oscillatory sawing devices, vibratory impaction devices, reamers, ultrasonic bone cutting devices, radio frequency ablation devices, reciprocating devices (such as a rasp or broach), and laser ablation systems. In some embodiments, the Resection Equipment 110 is held and operated by the surgeon during surgery. In other embodiments, the Effector Platform 105 may be used to hold the Resection Equipment 110 during use.

The Effector Platform 105 also can include a cutting guide or jig 105D that is used to guide saws or drills used to resect tissue during surgery. Such cutting guides 105D can be formed integrally as part of the Effector Platform 105 or robotic arm 105A or cutting guides can be separate structures that can be matingly and/or removably attached to the Effector Platform 105 or robotic arm 105A. The Effector Platform 105 or robotic arm 105A can be controlled by the CASS 100 to position a cutting guide or jig 105D adjacent to the patient's anatomy in accordance with a pre-operatively or intraoperatively developed surgical plan such that the cutting guide or jig will produce a precise bone cut in accordance with the surgical plan.

The Tracking System 115 uses one or more sensors to collect real-time position data that locates the patient's anatomy and surgical instruments. For example, for TKA procedures, the Tracking System may provide a location and orientation of the End Effector 105B during the procedure. In addition to positional data, data from the Tracking System 115 also can be used to infer velocity/acceleration of anatomy/instrumentation, which can be used for tool control. In some embodiments, the Tracking System 115 may use a tracker array attached to the End Effector 105B to determine the location and orientation of the End Effector 105B. The position of the End Effector 105B may be inferred based on the position and orientation of the Tracking System 115 and a known relationship in three-dimensional space between the Tracking System 115 and the End Effector 105B. Various types of tracking systems may be used in various embodiments of the present invention including, without limitation, Infrared (IR) tracking systems, electromagnetic (EM) tracking systems, video or image based tracking systems, and ultrasound registration and tracking systems. Using the data provided by the tracking system 115, the surgical computer 150 can detect objects and prevent collision. For example, the surgical computer 150 can prevent the robotic arm 105A and/or the End Effector 105B from colliding with soft tissue.

Any suitable tracking system can be used for tracking surgical objects and patient anatomy in the surgical theatre. For example, a combination of IR and visible light cameras can be used in an array. Various illumination sources, such as an IR LED light source, can illuminate the scene allowing three-dimensional imaging to occur. In some embodiments, this can include stereoscopic, tri-scopic, quad-scopic, etc. imaging. In addition to the camera array, which in some embodiments is affixed to a cart, additional cameras can be placed throughout the surgical theatre. For example, handheld tools or headsets worn by operators/surgeons can include imaging capability that communicates images back to a central processor to correlate those images with images captured by the camera array. This can give a more robust image of the environment for modeling using multiple perspectives. Furthermore, some imaging devices may be of suitable resolution or have a suitable perspective on the scene to pick up information stored in quick response (QR) codes or barcodes. This can be helpful in identifying specific objects not manually registered with the system. In some embodiments, the camera may be mounted on the robotic arm 105A.

In some embodiments, specific objects can be manually registered by a surgeon with the system preoperatively or intraoperatively. For example, by interacting with a user interface, a surgeon may identify the starting location for a tool or a bone structure. By tracking fiducial marks associated with that tool or bone structure, or by using other conventional image tracking modalities, a processor may track that tool or bone as it moves through the environment in a three-dimensional model.

In some embodiments, certain markers, such as fiducial marks that identify individuals, important tools, or bones in the theater may include passive or active identifiers that can be picked up by a camera or camera array associated with the tracking system. For example, an IR LED can flash a pattern that conveys a unique identifier to the source of that pattern, providing a dynamic identification mark. Similarly, one- or two-dimensional optical codes (barcode, QR code, etc.) can be affixed to objects in the theater to provide passive identification that can occur based on image analysis. If these codes are placed asymmetrically on an object, they also can be used to determine an orientation of an object by comparing the location of the identifier with the extents of an object in an image. For example, a QR code may be placed in a corner of a tool tray, allowing the orientation and identity of that tray to be tracked. Other tracking modalities are explained throughout. For example, in some embodiments, augmented reality (AR) headsets can be worn by surgeons and other staff to provide additional camera angles and tracking capabilities. In this case, the infrared/time of flight sensor data, which is predominantly used for hand/gesture detection, can build correspondence between the AR headset and the tracking system of the robotic system using sensor fusion techniques. This can be used to calculate a calibration matrix that relates the optical camera coordinate frame to the fixed holographic world frame.

In addition to optical tracking, certain features of objects can be tracked by registering physical properties of the object and associating them with objects that can be tracked, such as fiducial marks fixed to a tool or bone. For example, a surgeon may perform a manual registration process whereby a tracked tool and a tracked bone can be manipulated relative to one another. By impinging the tip of the tool against the surface of the bone, a three-dimensional surface can be mapped for that bone that is associated with a position and orientation relative to the frame of reference of that fiducial mark. By optically tracking the position and orientation (pose) of the fiducial mark associated with that bone, a model of that surface can be tracked with an environment through extrapolation.

The registration process that registers the CASS 100 to the relevant anatomy of the patient also can involve the use of anatomical landmarks, such as landmarks on a bone or cartilage. For example, the CASS 100 can include a 3D model of the relevant bone or joint and the surgeon can intraoperatively collect data regarding the location of bony landmarks on the patient's actual bone using a probe that is connected to the CASS. Bony landmarks can include, for example, the medial malleolus and lateral malleolus, the ends of the proximal femur and distal tibia, and the center of the hip joint. The CASS 100 can compare and register the location data of bony landmarks collected by the surgeon with the probe with the location data of the same landmarks in the 3D model. Alternatively, the CASS 100 can construct a 3D model of the bone or joint without pre-operative image data by using location data of bony landmarks and the bone surface that are collected by the surgeon using a CASS probe or other means. The registration process also can include determining various axes of a joint. For example, for a TKA the surgeon can use the CASS 100 to determine the anatomical and mechanical axes of the femur and tibia. The surgeon and the CASS 100 can identify the center of the hip joint by moving the patient's leg in a spiral direction (i.e., circumduction) so the CASS can determine where the center of the hip joint is located.

A Tissue Navigation System 120 (not shown in FIG. 1) provides the surgeon with intraoperative, real-time visualization for the patient's bone, cartilage, muscle, nervous, and/or vascular tissues surrounding the surgical area. Examples of systems that may be employed for tissue navigation include fluorescent imaging systems and ultrasound systems.

The Display 125 provides graphical user interfaces (GUIs) that display images collected by the Tissue Navigation System 120 as well other information relevant to the surgery. For example, in one embodiment, the Display 125 overlays image information collected from various modalities (e.g., CT, MRI, X-ray, fluorescent, ultrasound, etc.) collected pre-operatively or intra-operatively to give the surgeon various views of the patient's anatomy as well as real-time conditions. The Display 125 may include, for example, one or more computer monitors. As an alternative or supplement to the Display 125, one or more members of the surgical staff may wear an Augmented Reality (AR) Head Mounted Device (HMD). For example, in FIG. 1 the Surgeon 111 is wearing an AR HMD 155 that may, for example, overlay pre-operative image data on the patient or provide surgical planning suggestions. In one embodiment, a tracker array-mounted surgical tool could be detected by both the IR camera and an AR headset (HMD) using sensor fusion techniques without the need for any "intermediate" calibration rigs. This near-depth, time-of-flight sensing camera located in the HMD could be used for hand/gesture detection. The headset's sensor API can be used to expose IR and depth image data and carryout image processing using, for example, C++ with OpenCV. This approach allows the relationship between the CASS and the virtual coordinate frame to be determined and the headset sensor data (i.e., IR in combination with depth images) to isolate the CASS tracker arrays. The image processing system on the HMD can locate the surgical tool in a fixed holographic world frame and the CASS IR camera can locate the surgical tool relative to its camera coordinate frame. This relationship can be used to calculate a calibration matrix that relates the CASS IR camera coordinate frame to the fixed holographic world frame. This means that if a calibration matrix has previously been calculated, the surgical tool no longer needs to be visible to the AR headset. However, a recalculation may be necessary if the CASS camera is accidentally moved in the workflow. Various example uses of the AR HMD 155 in surgical procedures are detailed in the sections that follow.

Surgical Computer 150 provides control instructions to various components of the CASS 100, collects data from those components, and provides general processing for various data needed during surgery. In some embodiments, the Surgical Computer 150 is a general-purpose computer. In other embodiments, the Surgical Computer 150 may be a parallel computing platform that uses multiple central processing units (CPUs) or graphics processing units (GPU) to perform processing. In some embodiments, the Surgical Computer 150 is connected to a remote server over one or more computer networks (e.g., the Internet). The remote server can be used, for example, for storage of data or execution of computationally intensive processing tasks.

Various techniques generally known in the art can be used for connecting the Surgical Computer 150 to the other components of the CASS 100. Moreover, the computers can connect to the Surgical Computer 150 using a mix of technologies. For example, the End Effector 105B may connect to the Surgical Computer 150 over a wired (i.e., serial) connection. The Tracking System 115, Tissue Navigation System 120, and Display 125 can similarly be connected to the Surgical Computer 150 using wired connections. Alternatively, the Tracking System 115, Tissue Navigation System 120, and Display 125 may connect to the Surgical Computer 150 using wireless technologies such as, without limitation, Wi-Fi, Bluetooth, Near Field Communication (NFC), or ZigBee.

Robotic Arm

In some embodiments, the CASS 100 includes a robotic arm 105A that serves as an interface to stabilize and hold a variety of instruments used during the surgical procedure. For example, in the context of a hip surgery, these instruments may include, without limitation, retractors, a sagittal or reciprocating saw, the reamer handle, the cup impactor, the broach handle, and the stem inserter. The robotic arm 105A may have multiple degrees of freedom (like a Spider device) and have the ability to be locked in place (e.g., by a press of a button, voice activation, a surgeon removing a hand from the robotic arm, or other method).

In some embodiments, movement of the robotic arm 105A may be effectuated by use of a control panel built into the robotic arm system. For example, a display screen may include one or more input sources, such as physical buttons or a user interface having one or more icons, that direct movement of the robotic arm 105A. The surgeon or other healthcare professional may engage with the one or more input sources to position the robotic arm 105A when performing a surgical procedure.

A tool or an end effector 105B attached or integrated into a robotic arm 105A may include, without limitation, a burring device, a scalpel, a cutting device, a retractor, a joint tensioning device, or the like. In embodiments in which an end effector 105B is used, the end effector may be positioned at the end of the robotic arm 105A such that any motor control operations are performed within the robotic arm system. In embodiments in which a tool is used, the tool may be secured at a distal end of the robotic arm 105A, but motor control operation may reside within the tool itself.

The robotic arm 105A may be motorized internally to both stabilize the robotic arm, thereby preventing it from falling and hitting the patient, surgical table, surgical staff, etc., and to allow the surgeon to move the robotic arm without having to fully support its weight. While the surgeon is moving the robotic arm 105A, the robotic arm may provide some resistance to prevent the robotic arm from moving too fast or having too many degrees of freedom active at once. The position and the lock status of the robotic arm 105A may be tracked, for example, by a controller or the Surgical Computer 150.

In some embodiments, the robotic arm 105A can be moved by hand (e.g., by the surgeon) or with internal motors into its ideal position and orientation for the task being performed. In some embodiments, the robotic arm 105A may be enabled to operate in a "free" mode that allows the surgeon to position the arm into a desired position without being restricted. While in the free mode, the position and orientation of the robotic arm 105A may still be tracked as described above. In one embodiment, certain degrees of freedom can be selectively released upon input from user (e.g., surgeon) during specified portions of the surgical plan tracked by the Surgical Computer 150. Designs in which a robotic arm 105A is internally powered through hydraulics or motors or provides resistance to external manual motion through similar means can be described as powered robotic arms, while arms that are manually manipulated without power feedback, but which may be manually or automatically locked in place, may be described as passive robotic arms.

A robotic arm 105A or end effector 105B can include a trigger or other means to control the power of a saw or drill. Engagement of the trigger or other means by the surgeon can cause the robotic arm 105A or end effector 105B to transition from a motorized alignment mode to a mode where the saw or drill is engaged and powered on. Additionally, the CASS 100 can include a foot pedal (not shown) that causes the system to perform certain functions when activated. For example, the surgeon can activate the foot pedal to instruct the CASS 100 to place the robotic arm 105A or end effector 105B in an automatic mode that brings the robotic arm or end effector into the proper position with respect to the patient's anatomy in order to perform the necessary resections. The CASS 100 also can place the robotic arm 105A or end effector 105B in a collaborative mode that allows the surgeon to manually manipulate and position the robotic arm or end effector into a particular location. The collaborative mode can be configured to allow the surgeon to move the robotic arm 105A or end effector 105B medially or laterally, while restricting movement in other directions. As discussed, the robotic arm 105A or end effector 105B can include a cutting device (saw, drill, and burr) or a cutting guide or jig 105D that will guide a cutting device. In other embodiments, movement of the robotic arm 105A or robotically controlled end effector 105B can be controlled entirely by the CASS 100 without any, or with only minimal, assistance or input from a surgeon or other medical professional. In still other embodiments, the movement of the robotic arm 105A or robotically controlled end effector 105B can be controlled remotely by a surgeon or other medical professional using a control mechanism separate from the robotic arm or robotically controlled end effector device, for example using a joystick or interactive monitor or display control device.

A robotic arm 105A may be used for holding the retractor. For example, in one embodiment, the robotic arm 105A may be moved into the desired position by the surgeon. At that point, the robotic arm 105A may lock into place. In some embodiments, the robotic arm 105A is provided with data regarding the patient's position, such that if the patient moves, the robotic arm can adjust the retractor position accordingly. In some embodiments, multiple robotic arms may be used, thereby allowing multiple retractors to be held or for more than one activity to be performed simultaneously (e.g., retractor holding & reaming).

The robotic arm 105A may also be used to help stabilize the surgeon's hand while making a femoral neck cut. In this application, control of the robotic arm 105A may impose certain restrictions to prevent soft tissue damage from occurring. For example, in one embodiment, the Surgical Computer 150 tracks the position of the robotic arm 105A as it operates. If the tracked location approaches an area where tissue damage is predicted, a command may be sent to the robotic arm 105A causing it to stop. Alternatively, where the robotic arm 105A is automatically controlled by the Surgical Computer 150, the Surgical Computer may ensure that the robotic arm is not provided with any instructions that cause it to enter areas where soft tissue damage is likely to occur. The Surgical Computer 150 may impose certain restrictions on the surgeon to prevent the surgeon from reaming too far into the medial wall of the acetabulum or reaming at an incorrect angle or orientation.

In some embodiments, the robotic arm 105A may be used to hold a cup impactor at a desired angle or orientation during cup impaction. When the final position has been achieved, the robotic arm 105A may prevent any further seating to prevent damage to the pelvis.

The surgeon may use the robotic arm 105A to position the broach handle at the desired position and allow the surgeon to impact the broach into the femoral canal at the desired orientation. In some embodiments, once the Surgical Computer 150 receives feedback that the broach is fully seated, the robotic arm 105A may restrict the handle to prevent further advancement of the broach.

The robotic arm 105A may also be used for resurfacing applications. For example, the robotic arm 105A may stabilize the surgeon while using traditional instrumentation and provide certain restrictions or limitations to allow for proper placement of implant components (e.g., guide wire placement, chamfer cutter, sleeve cutter, plan cutter, etc.). Where only a burr is employed, the robotic arm 105A may stabilize the surgeon's handpiece and may impose restrictions on the handpiece to prevent the surgeon from removing unintended bone in contravention of the surgical plan.

The robotic arm 105A may be a passive arm. As an example, the robotic arm 105A may be a CIRQ robot arm available from Brainlab AG. CIRQ is a registered trademark of Brainlab AG, Olof-Palme-Str. 9 81829, München, FED REP of GERMANY. In one particular embodiment, the robotic arm 105A is an intelligent holding arm as disclosed in U.S. patent application Ser. No. 15/525,585 to Krinninger et al., U.S. patent application Ser. No. 15/561,042 to Nowatschin et al., U.S. patent application Ser. No. 15/561,048 to Nowatschin et al., and U.S. Pat. No. 10,342,636 to Nowatschin et al., the entire contents of each of which is herein incorporated by reference.

Surgical Procedure Data Generation and Collection

The various services that are provided by medical professionals to treat a clinical condition are collectively referred to as an "episode of care." For a particular surgical intervention, the episode of care can include three phases: pre-operative, intra-operative, and post-operative. During each phase, data is collected or generated that can be used to analyze the episode of care in order to understand various features of the procedure and identify patterns that may be used, for example, in training models to make decisions with minimal human intervention. The data collected over the episode of care may be stored at the Surgical Computer 150 or the Surgical Data Server 180 as a complete dataset. Thus, for each episode of care, a dataset exists that comprises all of the data collectively pre-operatively about the patient, all of the data collected or stored by the CASS 100 intra-operatively, and any post-operative data provided by the patient or by a healthcare professional monitoring the patient.

As explained in further detail, the data collected during the episode of care may be used to enhance performance of the surgical procedure or to provide a holistic understanding of the surgical procedure and the patient outcomes. For example, in some embodiments, the data collected over the episode of care may be used to generate a surgical plan. In one embodiment, a high-level, pre-operative plan is refined intra-operatively as data is collected during surgery. In this way, the surgical plan can be viewed as dynamically changing in real-time or near real-time as new data is collected by the components of the CASS 100. In other embodiments, pre-operative images or other input data may be used to develop a robust plan preoperatively that is simply executed during surgery. In this case, the data collected by the CASS 100 during surgery may be used to make recommendations that ensure that the surgeon stays within the pre-operative surgical plan. For example, if the surgeon is unsure how to achieve a certain prescribed cut or implant alignment, the Surgical Computer 150 can be queried for a recommendation. In still other embodiments, the pre-operative and intra-operative planning approaches can be combined such that a robust pre-operative plan can be dynamically modified, as necessary or desired, during the surgical procedure. In some embodiments, a biomechanics-based model of patient anatomy contributes simulation data to be considered by the CASS 100 in developing preoperative, intraoperative, and post-operative/rehabilitation procedures to optimize implant performance outcomes for the patient.

Aside from changing the surgical procedure itself, the data gathered during the episode of care may be used as an input to other procedures ancillary to the surgery. For example, in some embodiments, implants can be designed using episode of care data. Example data-driven techniques for designing, sizing, and fitting implants are described in U.S. Pat. No. 10,064,686, filed Aug. 15, 2011, and entitled "Systems and Methods for Optimizing Parameters for Orthopaedic Procedures"; U.S. Pat. No. 10,102,309, filed Jul. 20, 2012 and entitled "Systems and Methods for Optimizing Fit of an Implant to Anatomy"; and U.S. Pat. No. 8,078,440, filed Sep. 19, 2008 and entitled "Operatively Tuning Implants for Increased Performance," the entire contents of each of which are hereby incorporated by reference into this patent application.

Furthermore, the data can be used for educational, training, or research purposes. For example, using the network-based approach described below in FIG. 2C, other doctors or students can remotely view surgeries in interfaces that allow them to selectively view data as it is collected from the various components of the CASS 100. After the surgical procedure, similar interfaces may be used to "playback" a surgery for training or other educational purposes, or to identify the source of any issues or complications with the procedure.

Data acquired during the pre-operative phase generally includes all information collected or generated prior to the surgery. Thus, for example, information about the patient may be acquired from a patient intake form or electronic medical record (EMR). Examples of patient information that may be collected include, without limitation, patient demographics, diagnoses, medical histories, progress notes, vital signs, medical history information, allergies, and lab results. The pre-operative data may also include images related to the anatomical area of interest. These images may be captured, for example, using Magnetic Resonance Imaging (MRI), Computed Tomography (CT), X-ray, ultrasound, or any other modality known in the art. The pre-operative data may also comprise quality of life data captured from the patient. For example, in one embodiment, pre-surgery patients use a mobile application ("app") to answer questionnaires regarding their current quality of life. In some embodiments, preoperative data used by the CASS 100 includes demographic, anthropometric, cultural, or other specific traits about a patient that can coincide with activity levels and specific patient activities to customize the surgical plan to the patient. For example, certain cultures or demographics may be more likely to use a toilet that requires squatting on a daily basis.

Figure 2A:
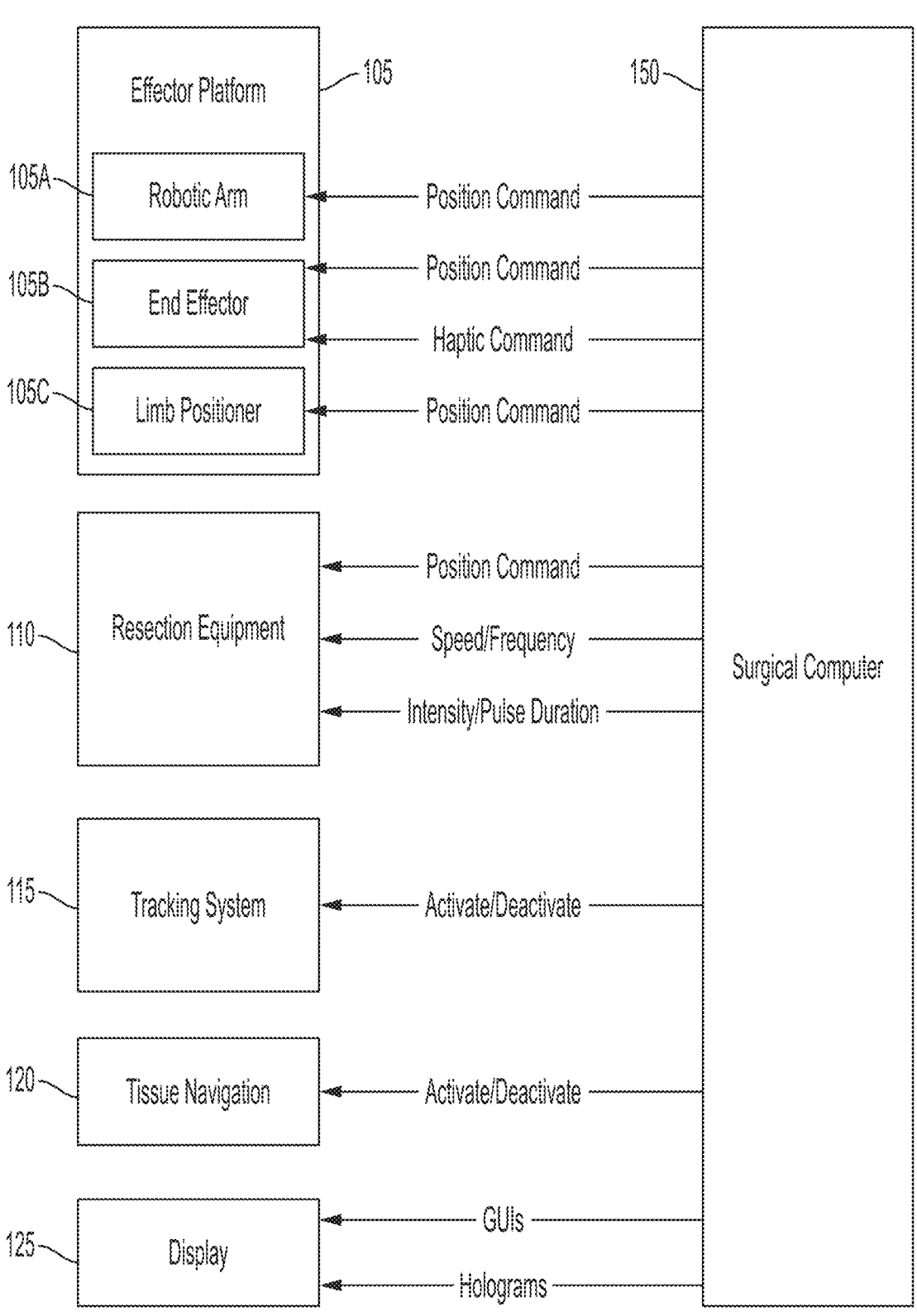
FIG. 2A depicts illustrative control instructions that a surgical computer provides to other components of a CASS in accordance with an embodiment.
Figure 2B:
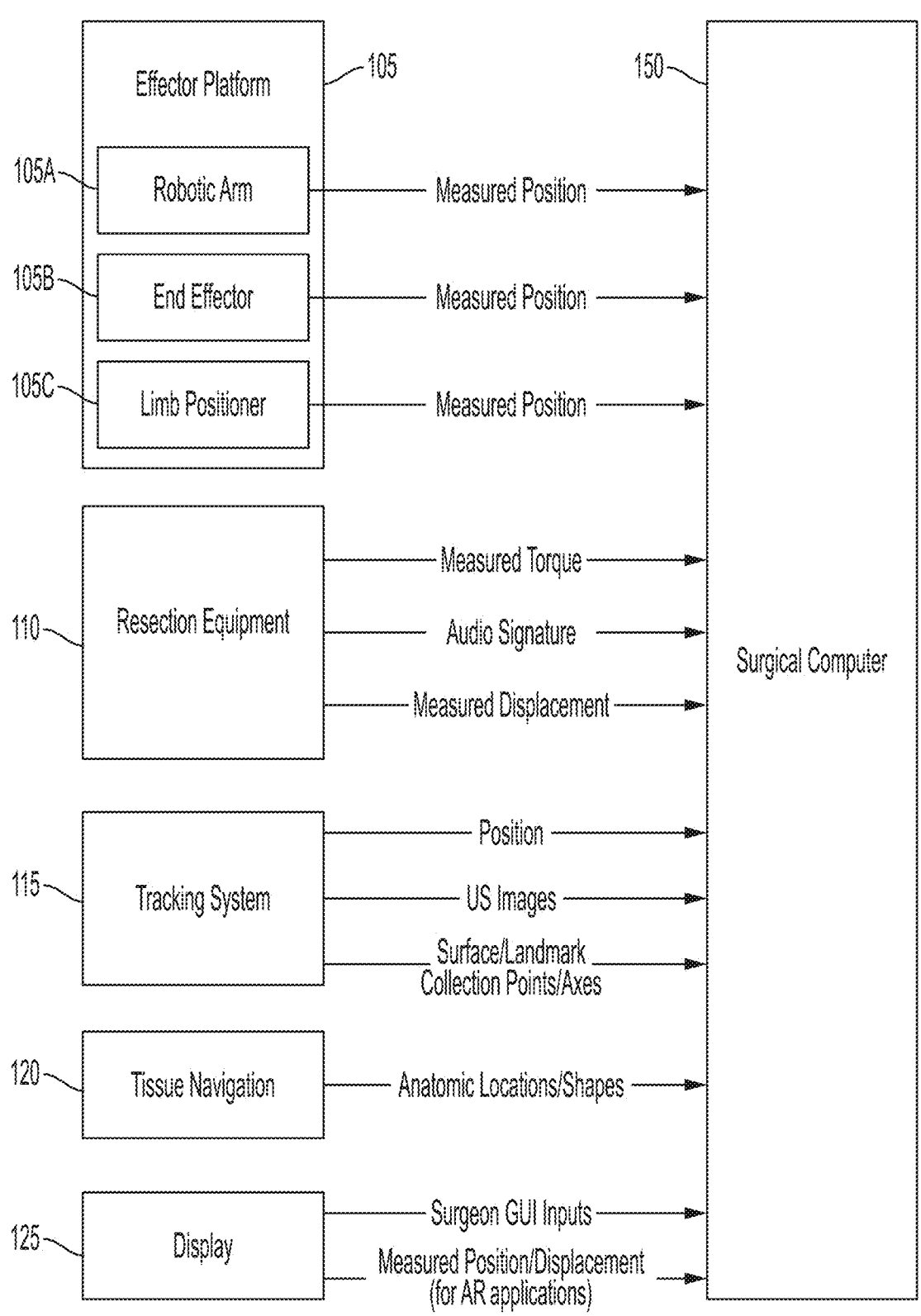
FIG. 2B depicts illustrative control instructions that components of a CASS provide to a surgical computer in accordance with an embodiment.

FIGS. 2A and 2B provide examples of data that may be acquired during the intra-operative phase of an episode of care. These examples are based on the various components of the CASS 100 described above with reference to FIG. 1; however, it should be understood that other types of data may be used based on the types of equipment used during surgery and their use.

FIG. 2A shows examples of some of the control instructions that the Surgical Computer 150 provides to other components of the CASS 100, according to some embodiments. Note that the example of FIG. 2A assumes that the components of the Effector Platform 105 are each controlled directly by the Surgical Computer 150. In embodiments where a component is manually controlled by the Surgeon 111, instructions may be provided on the Display 125 or AR HMD 155 instructing the Surgeon 111 how to move the component.

The various components included in the Effector Platform 105 are controlled by the Surgical Computer 150 providing position commands that instruct the component where to move within a coordinate system. In some embodiments, the Surgical Computer 150 provides the Effector Platform 105 with instructions defining how to react when a component of the Effector Platform 105 deviates from a surgical plan. These commands are referenced in FIG. 2A as "haptic" commands. For example, the End Effector 105B may provide a force to resist movement outside of an area where resection is planned. Other commands that may be used by the Effector Platform 105 include vibration and audio cues.

In some embodiments, the end effectors 105B of the robotic arm 105A are operatively coupled with cutting guide 105D. In response to an anatomical model of the surgical scene, the robotic arm 105A can move the end effectors 105B and the cutting guide 105D into position to match the location of the femoral or tibial cut to be performed in accordance with the surgical plan. This can reduce the likelihood of error, allowing the vision system and a processor utilizing that vision system to implement the surgical plan to place a cutting guide 105D at the precise location and orientation relative to the tibia or femur to align a cutting slot of the cutting guide with the cut to be performed according to the surgical plan. Then, a surgeon can use any suitable tool, such as an oscillating or rotating saw or drill to perform the cut (or drill a hole) with perfect placement and orientation because the tool is mechanically limited by the features of the cutting guide 105D. In some embodiments, the cutting guide 105D may include one or more pin holes that are used by a surgeon to drill and screw or pin the cutting guide into place before performing a resection of the patient tissue using the cutting guide. This can free the robotic arm 105A or ensure that the cutting guide 105D is fully affixed without moving relative to the bone to be resected. For example, this procedure can be used to make the first distal cut of the femur during a total knee arthroplasty. In some embodiments, where the arthroplasty is a hip arthroplasty, cutting guide 105D can be fixed to the femoral head or the acetabulum for the respective hip arthroplasty resection. It should be understood that any arthroplasty that utilizes precise cuts can use the robotic arm 105A and/or cutting guide 105D in this manner.

The Resection Equipment 110 is provided with a variety of commands to perform bone or tissue operations. As with the Effector Platform 105, position information may be provided to the Resection Equipment 110 to specify where it should be located when performing resection. Other commands provided to the Resection Equipment 110 may be dependent on the type of resection equipment. For example, for a mechanical or ultrasonic resection tool, the commands may specify the speed and frequency of the tool. For Radiofrequency Ablation (RFA) and other laser ablation tools, the commands may specify intensity and pulse duration.

Some components of the CASS 100 do not need to be directly controlled by the Surgical Computer 150; rather, the Surgical Computer 150 only needs to activate the component, which then executes software locally specifying the manner in which to collect data and provide it to the Surgical Computer 150. In the example of FIG. 2A, there are two components that are operated in this manner: the Tracking System 115 and the Tissue Navigation System 120.

The Surgical Computer 150 provides the Display 125 with any visualization that is needed by the Surgeon 111 during surgery. For monitors, the Surgical Computer 150 may provide instructions for displaying images, GUIs, etc. using techniques known in the art. The display 125 can include various portions of the workflow of a surgical plan. During the registration process, for example, the display 125 can show a preoperatively constructed 3D bone model and depict the locations of the probe as the surgeon uses the probe to collect locations of anatomical landmarks on the patient. The display 125 can include information about the surgical target area. For example, in connection with a TKA, the display 125 can depict the mechanical and anatomical axes of the femur and tibia. The display 125 can depict *varus* and valgus angles for the knee joint based on a surgical plan, and the CASS 100 can depict how such angles will be affected if contemplated revisions to the surgical plan are made. Accordingly, the display 125 is an interactive interface that can dynamically update and display how changes to the surgical plan would impact the procedure and the final position and orientation of implants installed on bone.

As the workflow progresses to preparation of bone cuts or resections, the display 125 can depict the planned or recommended bone cuts before any cuts are performed. The surgeon 111 can manipulate the image display to provide different anatomical perspectives of the target area and can have the option to alter or revise the planned bone cuts based on intraoperative evaluation of the patient. The display 125 can depict how the chosen implants would be installed on the bone if the planned bone cuts are performed. If the surgeon 111 choses to change the previously planned bone cuts, the display 125 can depict how the revised bone cuts would change the position and orientation of the implant when installed on the bone.

The display 125 can provide the surgeon 111 with a variety of data and information about the patient, the planned surgical intervention, and the implants. Various patient-specific information can be displayed, including real-time data concerning the patient's health such as heart rate, blood pressure, etc. The display 125 also can include information about the anatomy of the surgical target region including the location of landmarks, the current state of the anatomy (e.g., whether any resections have been made, the depth and angles of planned and executed bone cuts), and future states of the anatomy as the surgical plan progresses. The display 125 also can provide or depict additional information about the surgical target region. For a TKA, the display 125 can provide information about the gaps (e.g., gap balancing) between the femur and tibia and how such gaps will change if the planned surgical plan is carried out. For a TKA, the display 125 can provide additional relevant information about the knee joint such as data about the joint's tension (e.g., ligament laxity) and information concerning rotation and alignment of the joint. The display 125 can depict how the planned implants' locations and positions will affect the patient as the knee joint is flexed. The display 125 can depict how the use of different implants or the use of different sizes of the same implant will affect the surgical plan and preview how such implants will be positioned on the bone. The CASS 100 can provide such information for each of the planned bone resections in a TKA or THA. In a TKA, the CASS 100 can provide robotic control for one or more of the planned bone resections. For example, the CASS 100 can provide robotic control only for the initial distal femur cut, and the surgeon 111 can manually perform other resections (anterior, posterior and chamfer cuts) using conventional means, such as a 4-in-1 cutting guide or jig 105D.

The display 125 can employ different colors to inform the surgeon of the status of the surgical plan. For example, un-resected bone can be displayed in a first color, resected bone can be displayed in a second color, and planned resections can be displayed in a third color. Implants can be superimposed onto the bone in the display 125, and implant colors can change or correspond to different types or sizes of implants.

The information and options depicted on the display 125 can vary depending on the type of surgical procedure being performed. Further, the surgeon 111 can request or select a particular surgical workflow display that matches or is consistent with his or her surgical plan preferences. For example, for a surgeon 111 who typically performs the tibial cuts before the femoral cuts in a TKA, the display 125 and associated workflow can be adapted to take this preference into account. The surgeon 111 also can preselect that certain steps be included or deleted from the standard surgical workflow display. For example, if a surgeon 111 uses resection measurements to finalize an implant plan but does not analyze ligament gap balancing when finalizing the implant plan, the surgical workflow display can be organized into modules, and the surgeon can select which modules to display and the order in which the modules are provided based on the surgeon's preferences or the circumstances of a particular surgery. Modules directed to ligament and gap balancing, for example, can include pre- and post-resection ligament/gap balancing, and the surgeon 111 can select which modules to include in their default surgical plan workflow depending on whether they perform such ligament and gap balancing before or after (or both) bone resections are performed.

For more specialized display equipment, such as AR HMDs, the Surgical Computer 150 may provide images, text, etc. using the data format supported by the equipment. For example, if the Display 125 is a holography device such as the Microsoft HoloLens™ or Magic Leap One™, the Surgical Computer 150 may use the HoloLens Application Program Interface (API) to send commands specifying the position and content of holograms displayed in the field of view of the Surgeon 111.

In some embodiments, one or more surgical planning models may be incorporated into the CASS 100 and used in the development of the surgical plans provided to the surgeon 111. The term "surgical planning model" refers to software that simulates the biomechanics performance of anatomy under various scenarios to determine the optimal way to perform cutting and other surgical activities. For example, for knee replacement surgeries, the surgical planning model can measure parameters for functional activities, such as deep knee bends, gait, etc., and select cut locations on the knee to optimize implant placement. One example of a surgical planning model is the LIFEMOD™ simulation software from SMITH AND NEPHEW, INC. In some embodiments, the Surgical Computer 150 includes computing architecture that allows full execution of the surgical planning model during surgery (e.g., a GPU-based parallel processing environment). In other embodiments, the Surgical Computer 150 may be connected over a network to a remote computer that allows such execution, such as a Surgical Data Server 180 (see FIG. 2C). As an alternative to full execution of the surgical planning model, in some embodiments, a set of transfer functions are derived that simplify the mathematical operations captured by the model into one or more predictor equations. Then, rather than execute the full simulation during surgery, the predictor equations are used. Further details on the use of transfer functions are described in WIPO Publication No. 2020/037308, filed Aug. 19, 2019, entitled "Patient Specific Surgical Method and System," the entirety of which is incorporated herein by reference.

FIG. 2B shows examples of some of the types of data that can be provided to the Surgical Computer 150 from the various components of the CASS 100. In some embodiments, the components may stream data to the Surgical Computer 150 in real-time or near real-time during surgery. In other embodiments, the components may queue data and send it to the Surgical Computer 150 at set intervals (e.g., every second). Data may be communicated using any format known in the art. Thus, in some embodiments, the components all transmit data to the Surgical Computer 150 in a common format. In other embodiments, each component may use a different data format, and the Surgical Computer 150 is configured with one or more software applications that enable translation of the data.

In general, the Surgical Computer 150 may serve as the central point where CASS data is collected. The exact content of the data will vary depending on the source. For example, each component of the Effector Platform 105 provides a measured position to the Surgical Computer 150. Thus, by comparing the measured position to a position originally specified by the Surgical Computer 150 (see FIG. 2B), the Surgical Computer can identify deviations that take place during surgery.

The Resection Equipment 110 can send various types of data to the Surgical Computer 150 depending on the type of equipment used. Example data types that may be sent include the measured torque, audio signatures, and measured displacement values. Similarly, the Tracking Technology 115 can provide different types of data depending on the tracking methodology employed. Example tracking data types include position values for tracked items (e.g., anatomy, tools, etc.), ultrasound images, and surface or landmark collection points or axes. The Tissue Navigation System 120 provides the Surgical Computer 150 with anatomic locations, shapes, etc. as the system operates.

Although the Display 125 generally is used for outputting data for presentation to the user, it may also provide data to the Surgical Computer 150. For example, for embodiments where a monitor is used as part of the Display 125, the Surgeon 111 may interact with a GUI to provide inputs which are sent to the Surgical Computer 150 for further processing. For AR applications, the measured position and displacement of the HMD may be sent to the Surgical Computer 150 so that it can update the presented view as needed.

During the post-operative phase of the episode of care, various types of data can be collected to quantify the overall improvement or deterioration in the patient's condition as a result of the surgery. The data can take the form of, for example, self-reported information reported by patients via questionnaires. For example, in the context of a knee replacement surgery, functional status can be measured with an Oxford Knee Score questionnaire, and the post-operative quality of life can be measured with a EQ5D-5L questionnaire. Other examples in the context of a hip replacement surgery may include the Oxford Hip Score, Harris Hip Score, and WOMAC (Western Ontario and McMaster Universities Osteoarthritis index). Such questionnaires can be administered, for example, by a healthcare professional directly in a clinical setting or using a mobile app that allows the patient to respond to questions directly. In some embodiments, the patient may be outfitted with one or more wearable devices that collect data relevant to the surgery. For example, following a knee surgery, the patient may be outfitted with a knee brace that includes sensors that monitor knee positioning, flexibility, etc. This information can be collected and transferred to the patient's mobile device for review by the surgeon to evaluate the outcome of the surgery and address any issues. In some embodiments, one or more cameras can capture and record the motion of a patient's body segments during specified activities postoperatively. This motion capture can be compared to a biomechanics model to better understand the functionality of the patient's joints and better predict progress in recovery and identify any possible revisions that may be needed.

The post-operative stage of the episode of care can continue over the entire life of a patient. For example, in some embodiments, the Surgical Computer 150 or other components comprising the CASS 100 can continue to receive and collect data relevant to a surgical procedure after the procedure has been performed. This data may include, for example, images, answers to questions, "normal" patient data (e.g., blood type, blood pressure, conditions, medications, etc.), biometric data (e.g., gait, etc.), and objective and subjective data about specific issues (e.g., knee or hip joint pain). This data may be explicitly provided to the Surgical Computer 150 or other CASS component by the patient or the patient's physician(s). Alternatively, or additionally, the Surgical Computer 150 or other CASS component can monitor the patient's EMR and retrieve relevant information as it becomes available. This longitudinal view of the patient's recovery allows the Surgical Computer 150 or other CASS component to provide a more objective analysis of the patient's outcome to measure and track success or lack of success for a given procedure. For example, a condition experienced by a patient long after the surgical procedure can be linked back to the surgery through a regression analysis of various data items collected during the episode of care. This analysis can be further enhanced by performing the analysis on groups of patients that had similar procedures and/or have similar anatomies.

In some embodiments, data is collected at a central location to provide for easier analysis and use. Data can be manually collected from various CASS components in some instances. For example, a portable storage device (e.g., USB stick) can be attached to the Surgical Computer 150 into order to retrieve data collected during surgery. The data can then be transferred, for example, via a desktop computer to the centralized storage. Alternatively, in some embodiments, the Surgical Computer 150 is connected directly to the centralized storage via a Network 175 as shown in FIG. 2C.

Figure 2C:
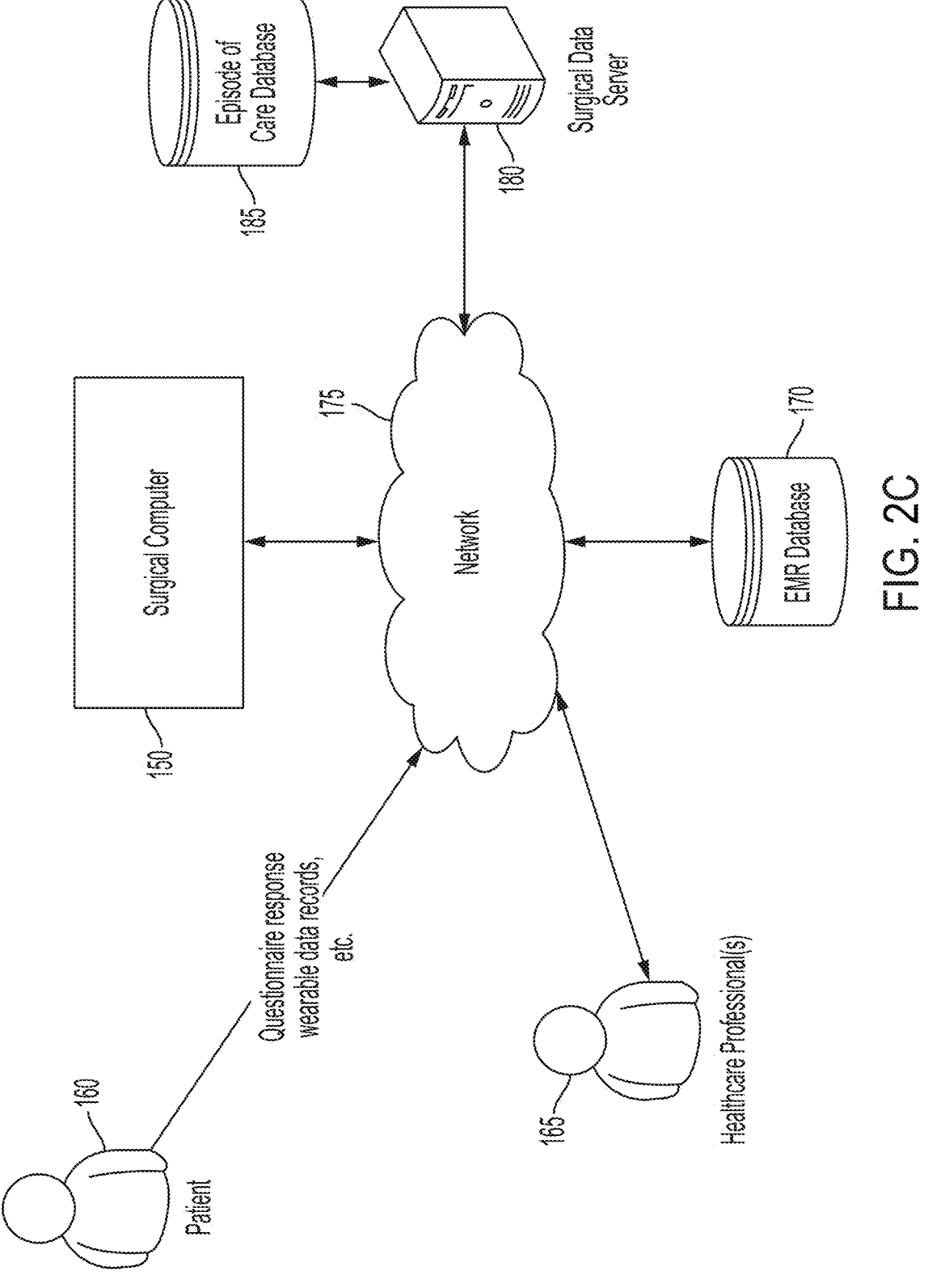
FIG. 2C depicts an illustrative implementation in which a surgical computer is connected to a surgical data server via a network in accordance with an embodiment.

FIG. 2C illustrates a "cloud-based" implementation in which the Surgical Computer 150 is connected to a Surgical Data Server 180 via a Network 175. This Network 175 may be, for example, a private intranet or the Internet. In addition to the data from the Surgical Computer 150, other sources can transfer relevant data to the Surgical Data Server 180. The example of FIG. 2C shows three additional data sources: the Patient 160, Healthcare Professional(s) 165, and an EMR Database 170. Thus, the Patient 160 can send pre-operative and post-operative data to the Surgical Data Server 180, for example, using a mobile app. The Healthcare Professional(s) 165 includes the surgeon and his or her staff as well as any other professionals working with Patient 160 (e.g., a personal physician, a rehabilitation specialist, etc.). It should also be noted that the EMR Database 170 may be used for both pre-operative and post-operative data. For example, assuming that the Patient 160 has given adequate permissions, the Surgical Data Server 180 may collect the EMR of the Patient pre-surgery. Then, the Surgical Data Server 180 may continue to monitor the EMR for any updates post-surgery.

At the Surgical Data Server 180, an Episode of Care Database 185 is used to store the various data collected over a patient's episode of care. The Episode of Care Database 185 may be implemented using any technique known in the art. For example, in some embodiments, a SQL-based database may be used where all of the various data items are structured in a manner that allows them to be readily incorporated in two SQL's collection of rows and columns. However, in other embodiments a No-SQL database may be employed to allow for unstructured data, while providing the ability to rapidly process and respond to queries. As is understood in the art, the term "No-SQL" is used to define a class of data stores that are non-relational in their design.

Various types of No-SQL databases may generally be grouped according to their underlying data model. These groupings may include databases that use column-based data models (e.g., Cassandra), document-based data models (e.g., MongoDB), key-value based data models (e.g., Redis), and/or graph-based data models (e.g., Allego). Any type of No-SQL database may be used to implement the various embodiments described herein and, in some embodiments, the different types of databases may support the Episode of Care Database 185.

Data can be transferred between the various data sources and the Surgical Data Server 180 using any data format and transfer technique known in the art. It should be noted that the architecture shown in FIG. 2C allows transmission from the data source to the Surgical Data Server 180, as well as retrieval of data from the Surgical Data Server 180 by the data sources. For example, as explained in detail below, in some embodiments, the Surgical Computer 150 may use data from past surgeries, machine learning models, etc. to help guide the surgical procedure.

In some embodiments, the Surgical Computer 150 or the Surgical Data Server 180 may execute a de-identification process to ensure that data stored in the Episode of Care Database 185 meets Health Insurance Portability and Accountability Act (HIPAA) standards or other requirements mandated by law. HIPAA provides a list of certain identifiers that must be removed from data during de-identification. The aforementioned de-identification process can scan for these identifiers in data that is transferred to the Episode of Care Database 185 for storage. For example, in one embodiment, the Surgical Computer 150 executes the de-identification process just prior to initiating transfer of a particular data item or set of data items to the Surgical Data Server 180. In some embodiments, a unique identifier is assigned to data from a particular episode of care to allow for re-identification of the data if necessary.

Although FIGS. 2A-C discuss data collection in the context of a single episode of care, it should be understood that the general concept can be extended to data collection from multiple episodes of care. For example, surgical data may be collected over an entire episode of care each time a surgery is performed with the CASS 100 and stored at the Surgical Computer 150 or at the Surgical Data Server 180. As explained in further detail below, a robust database of episode of care data allows the generation of optimized values, measurements, distances, or other parameters and other recommendations related to the surgical procedure. In some embodiments, the various datasets are indexed in the database or other storage medium in a manner that allows for rapid retrieval of relevant information during the surgical procedure. For example, in one embodiment, a patient-centric set of indices may be used so that data pertaining to a particular patient or a set of patients similar to a particular patient can be readily extracted. This concept can be similarly applied to surgeons, implant characteristics, CASS component versions, etc.

Further details of the management of episode of care data are described in U.S. patent application Ser. No. 16/847,183, filed Apr. 13, 2020, published as U.S. Publication No. 2020/0243199, and entitled "METHODS AND SYSTEMS FOR PROVIDING AN EPISODE OF CARE," the entirety of which is incorporated herein by reference.

Tensioner Tools for Assessing Laxity of Joint

Figure 3:
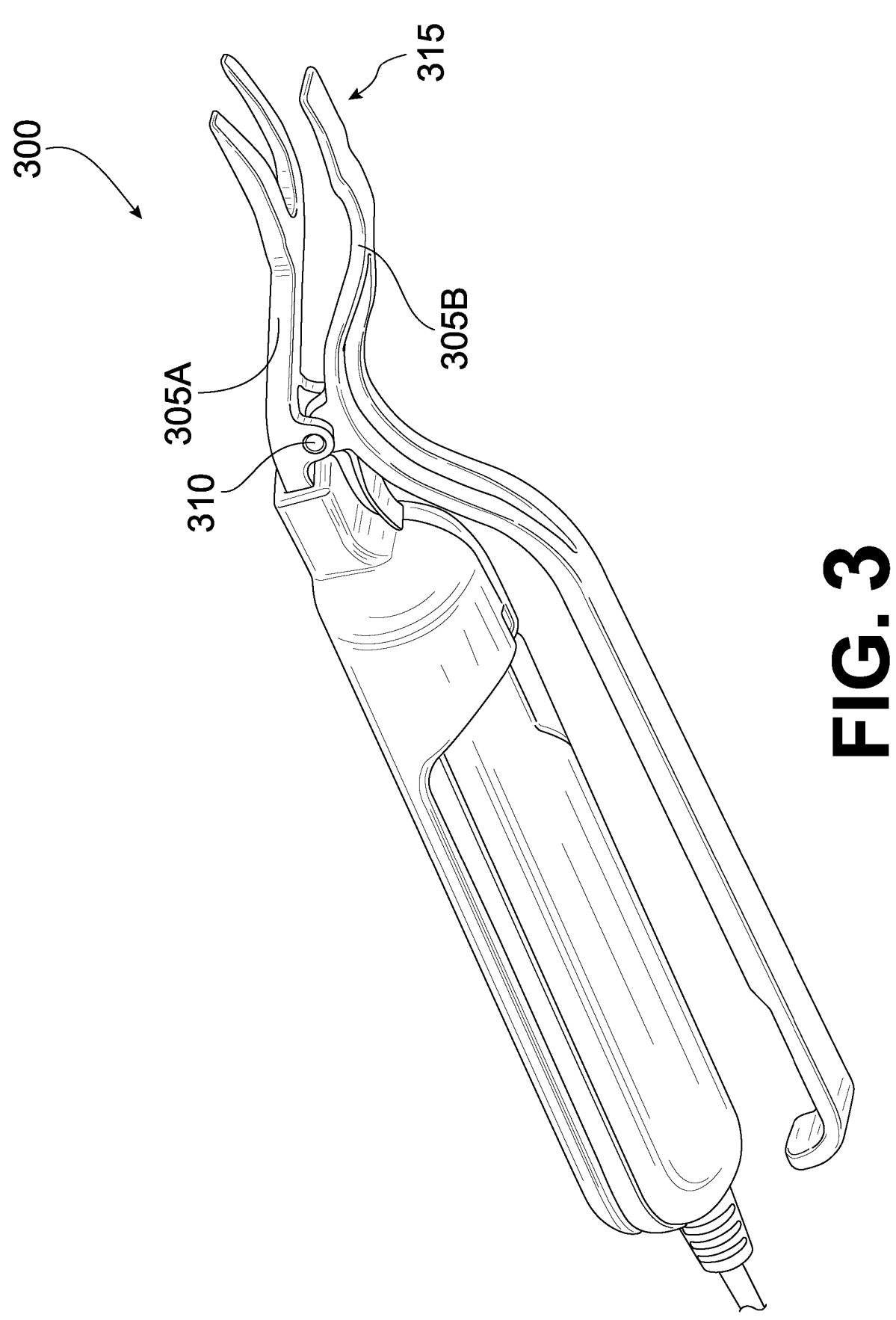
FIG. 3 depicts a tensioner tool in accordance with an embodiment.

Referring now to FIG. 3, a tensioner tool is depicted in accordance with an embodiment. The tensioner tool 300 may further be incorporated within a CASS (e.g., CASS 100 shown in FIG. 1). The tensioner tool 300 comprises a first arm 305A and a second arm 305B coupled by a pivot 310 located along the length of the arms 305. The first arm 305A and the second arm 305B form an insertion portion 315 at their distal ends, which may include a two-pronged tip of the first arm 305A and a one-pronged tip of the second arm 305B. The two-pronged design of the second arm 305B may be configured for engaging the femur or a femur component and cradling a condyle of the femur. The two-pronged tip may self-center upon the condyle by sliding along the surface of the condyle as the insertion tip is placed and/or retracted.

The tensioner tool 300 may be moved between a closed configuration and an open configuration by pivotal movement of the arms 305A-B about the pivot 310. The pivot 310 is configured to allow manual separation of the insertion portion 315 by applying force to the handles of the arms 305A-B.

The tensioner tool 300 may comprise one or more force sensors located upon one of the arms 305A-B to measure the force applied to the joint. In some embodiments, the one or more force sensors are located distally of the pivot 310. For example, the one or more force sensors may be adjacent to the insertion portion 315. However, a force sensor may be placed in additional or alternative locations upon the arms. In some embodiments, the tensioner tool 300 includes an array of force sensors. Additional locations and arrangements of force sensors will be apparent to a person having an ordinary level of skill in the art. In some embodiments, the one or more force sensors comprise one or more strain gauges. However, any types of force sensors could alternatively or additionally be utilized with the tensioner tool 300.

In some embodiments, the tensioner tool 300 comprises one or more positional sensors in order to facilitate calculation of a tip distance between the tips of the arms 305A-B, i.e., the insertion portion 315, which corresponds to a distraction distance during distraction of a joint. The positional sensor may be contained within the joint of pivot 310 and configured to measure a rotational displacement at the pivot. The pivot 310 has a known spatial relationship with the distal end of the tensioner tool. As such, the distraction distance may be calculated according to the equation:

$$\text{distraction distance} = \sqrt{L_{P1}^2 + L_{P2}^2 - 2L_{P1}L_{P2}\cos(\theta_{rot})}$$

where $L_{P1}$ is a first prong length (i.e., the length of the first arm 305A from the pivot 310 to the corresponding tip, $L_{P2}$ is a second prong length (i.e., the length of the second arm 305B from the pivot 310 to the corresponding tip), and $\theta_{rot}$ is the angular displacement measured by the positional sensor at the pivot 310.

In some embodiments, the one or more positional sensors comprise one or more rotary encoders. The rotary encoder may be inserted within the pivot 310 in order to measure rotational displacement. Other types of rotational sensors could alternatively or additionally be utilized. In some embodiments, the one or more positional sensors may include a rotary potentiometer. In some embodiments, the one or more positional sensors may include an orientation sensor located along the length of the arms. For example, the one or more positional sensors may comprise an inertial measurement unit configured to measure a change in the orientation of the arms. In some embodiments, the tensioner tool 300 includes a plurality of positional sensors at the pivot 310 to more accurately calculate the distraction distance. In some embodiments, the one or more positional sensors further include one or more sensors configured to measure a separation distance at a location along the arms 305A-B, which may be used to calculate the angular displacement and/or the distraction distance based on the known geometry of the tensioner tool 300. Additional locations and arrangements of positional sensors will be apparent to one having an ordinary level of skill in the art.

In some embodiments, the sensors of the tensioner tool 300 may directly or indirectly communicate with a processor, e.g., the surgical computer 150 of the CASS 100, to perform calculations based on the force and/or distance measurements. For example, a gap distance of the joint for a particular applied force or force range may be determined by the processor.

Further details of tensioner tools are described in International Patent Application No. PCT/US2021/029355, filed Apr. 27, 2021, published as International Patent Application Publication No. 2021/222216, and entitled "KNEE TENSIONER WITH DIGITAL FORCE AND DISPLACEMENT SENSING," the entirety of which is incorporated herein by reference.

Device for Assessing Laxity of Joint

As discussed herein, it would be advantageous to have a system for measuring and assessing a joint laxity that facilitates a gap profile less than a thickness of the tensioner tool. Ideally, the system would enable "zero-thickness" by allowing insertion of a tensioner tool without placing a minimum gap between the joint components. Such a system may enable surgeons to measure and implement smaller gaps during post-operative trialing to provide improved surgical outcomes.

Figure 4A:
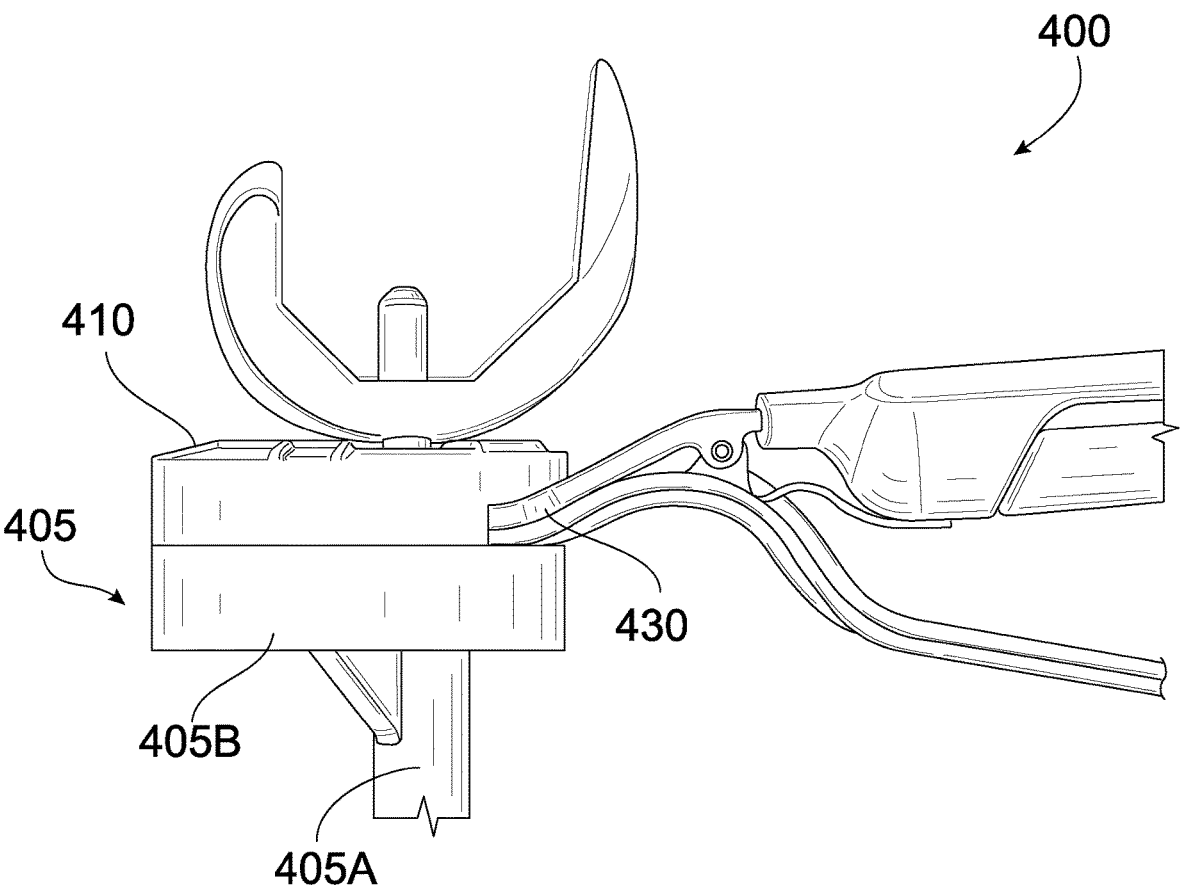
FIGS. 4A-4B depict side views of an illustrative device for assessing laxity of a joint in accordance with an embodiment.
Figure 4B:
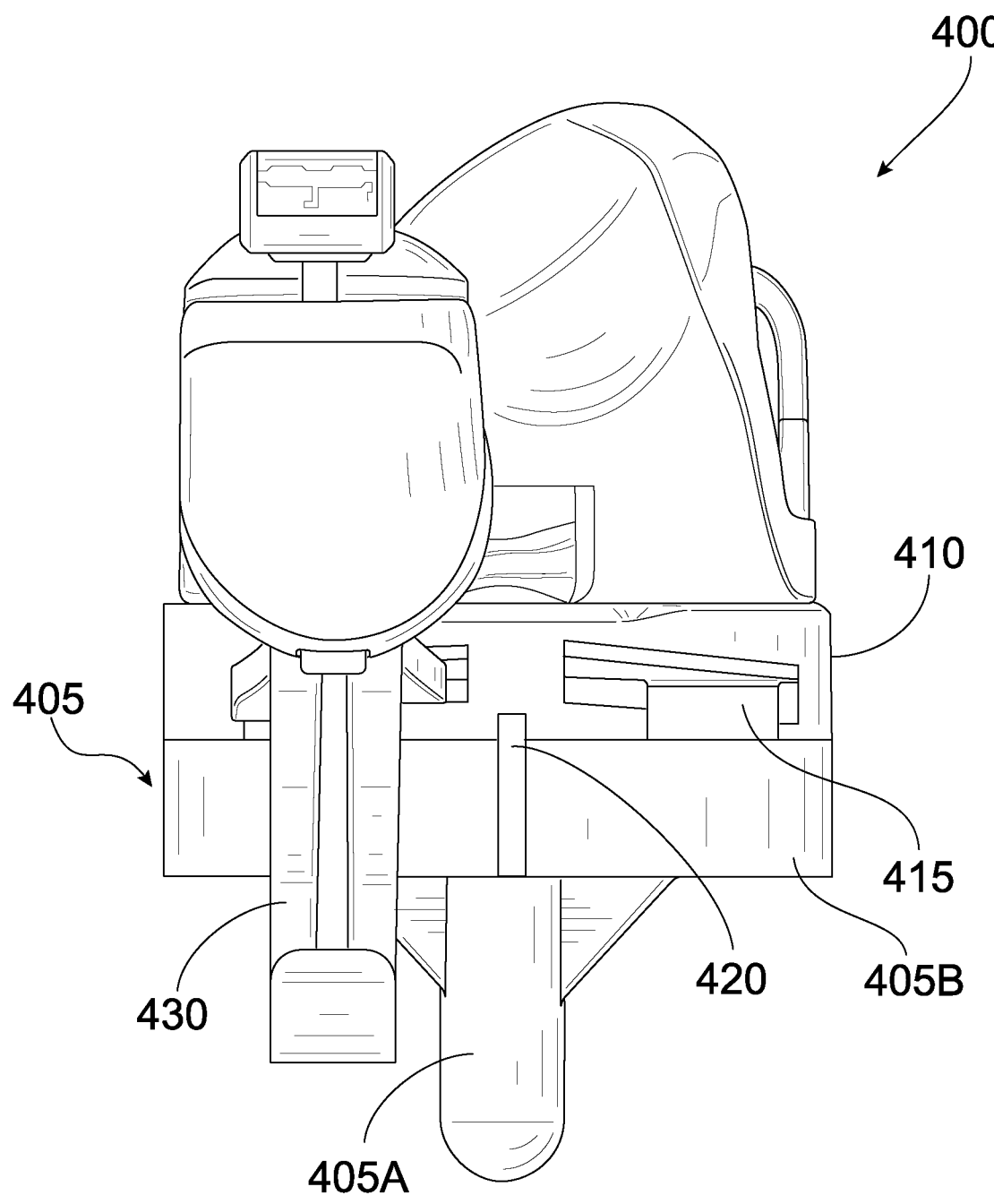

FIGS. 4A-4B depict side views of an illustrative device for assessing laxity of a joint in accordance with an embodiment. As shown, the device 400 comprises a base plate 405, superior spacer 410, and a cavity 415 defined between the base plate 405 and the superior spacer 410. In some embodiments, the superior spacer 410 is in contact with the base plate 405 in a first position and spaced from the base plate 405 in a second position.

The base plate 405 may be configured to be coupled to a first bone of the joint, e.g., a tibia. In some embodiments, the base plate 405 comprises a lower stem 405A configured to couple with the tibia of the joint and an upper platform 405B connected to the lower stem 405A. In some embodiments, the base plate 405 may be applied to the tibia such that the upper platform 405B extends away from the tibia. In some embodiments, the upper platform 405B defines a superior surface that faces a second bone of the joint, e.g., a femur. As further described, the superior surface may be configured to receive the superior spacer 410.

Figure 5:
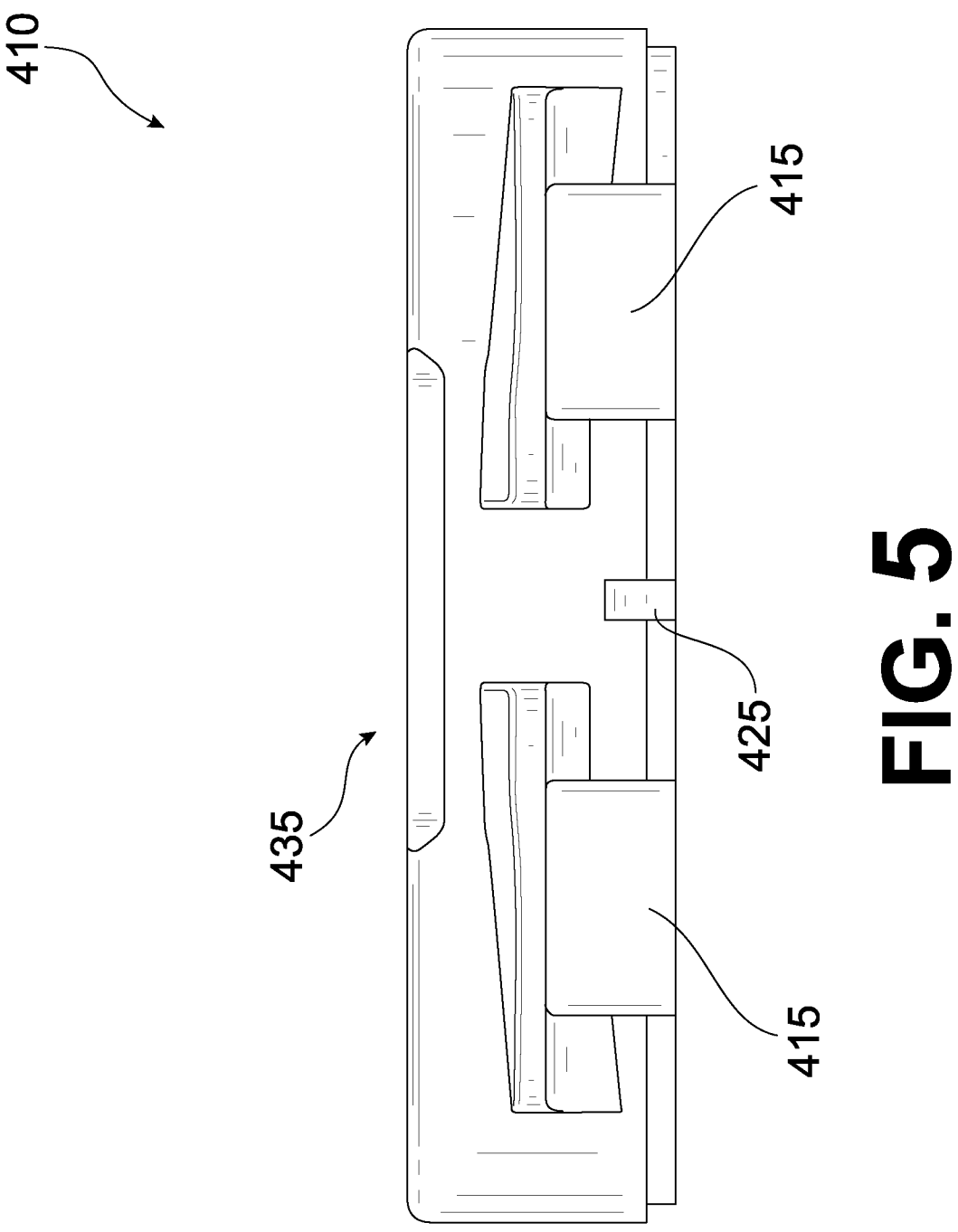
FIG. 5 depicts an isolated view of a superior spacer of the device in accordance with an embodiment.

FIG. 5 depicts an isolated view of a superior spacer 410 of the device 400 in accordance with an embodiment. The superior spacer 410 may be coupled to the base plate 405. In some embodiments, as shown in FIGS. 4A-4B, the superior spacer 410 is coupled to the upper platform 405B of the base plate 405. For example, the superior spacer 410 may be disposed on the superior surface of the upper platform 405B. In some embodiments, the superior spacer 410 is coupled to the upper platform 405B of the base plate 405 in an adjustable or movable manner. In some embodiments, the upper platform 405B and the superior spacer 410 have a matching geometry as further described herein. In some embodiments, at least the superior surface of the upper platform 405B and an inferior surface of the superior spacer 410 have complementary features such that the surfaces may be aligned and joined to one another as shown in FIG. 4A.

In some embodiments, the upper platform 405B and the superior spacer 410 have at least a matching cross-sectional geometry. For example, a transverse cross-sectional geometry (i.e., a horizontal cross-sectional geometry as seen in FIGS. 4A-4B and 5) of the upper platform 405B may substantially match a transverse cross-sectional geometry of the superior spacer 410. For example, the upper platform 405B and the superior spacer 410 may have substantially the same cross-sectional area and/or cross-sectional shape. For example, as shown in FIGS. 4A-4B, a horizontal cross-section of the upper platform 405B may yield substantially the same shape as a horizontal cross-section of the superior spacer 410. For example, the upper platform 405B and the superior spacer 410 may have the same or similar footprint. Accordingly, the upper platform 405B and the superior spacer 410 may be aligned and joined to one another as shown in FIG. 4A such that the combined footprint of the upper platform 405B and the superior spacer 410 is substantially equal to the footprint of either one of the upper platform 405B and the superior spacer 410.

In some embodiments, the upper platform 405B and the superior spacer 410 have complementary mating features to couple the superior spacer 410 to the upper platform 405B. For example, as shown in FIG. 4B, the upper platform 405B may comprise one or more protrusions 420 and/or other surface features extending from the superior surface. Likewise, as shown in FIG. 5, the superior spacer 410 may have one or more grooves or depressions 425 and/or other surface features disposed on the inferior surface. The grooves 425 may be complementary to the protrusions 420 such that the protrusions 420 may mate with the grooves 425 to couple the superior spacer 410 to the upper platform 405B. While an exemplary embodiment of complementary features is described, it should be understood that any type of mating features for securing complementary components may be utilized herein as would be known to a person having an ordinary level of skill in the art. The complementary mating features may lock movement between the upper platform 405B and the superior spacer 410 in one or more degrees of freedom to couple the components in a stable manner. Nonetheless, the complementary mating features may allow for movement between the upper platform 405B and the superior spacer 410 to enable movement between the first position and the second position as further described herein. For example, the superior spacer 410 may be coupled to the upper platform 405B in an adjustable manner such that the superior spacer 410 may be lifted or separated from the superior surface by a tensioner tool as further described herein.

Referring once again to FIG. 5, the device 400 may comprise one or more cavities 415 formed within the superior spacer 410. In some embodiments, the device 400 comprises a single cavity 415. In some embodiments, the device 400 comprises two cavities 415. Each cavity 415 may extend inwardly from the inferior surface of the superior spacer 410. Accordingly, each cavity 415 may be defined between the superior spacer 410 and the superior surface of the upper platform 405B as shown in FIG. 4B. In some embodiments, each cavity 415 is configured to receive a tensioner tool 430 as shown in FIG. 4A. In some embodiments, the tensioner tool 430 may be a tensioner tool 300 as described with respect to FIG. 3.

In some embodiments, the one or more cavities 415 may be configured to align with medial and/or lateral compartments of the joint. Accordingly, each cavity 415 may be engaged by the tensioner tool 430 to distract the corresponding portion of the joint individually. In some embodiments, a cavity 415 may be configured to align with the center of the joint (e.g., in the case of a single cavity 415). Accordingly, the cavity 415 may be engaged by the tensioner tool 430 to distract the joint as a whole including the medial and lateral portions simultaneously.

In some embodiments, each cavity 415 may be sized and shaped to receive and retain the tensioner tool 430 therein. For example, the cavity 415 may be fitted to a particular tensioner tool 430 in order to prevent unwanted movement or dislodging of the tensioner tool 430 during tensioning. However, in some embodiments, the cavity 415 may be sized and shaped to accommodate a wide variety of different tensioner tools 430, and the size and shape of the cavity 415 may be selected to sufficiently prevent unwanted movement or dislodging of the variety of tensioner tools contemplated for use with the device 400.

In some embodiments, the cavity 415 comprises a geometry configured to mate with the tensioner tool 430. As shown in FIG. 4A, the tensioner tool 430 may comprise a pair of pivoting arms, i.e., an upper arm and a lower arm. Accordingly, in some embodiments, the surfaces of the upper platform 405B and/or the superior spacer 410 that define the cavity 415 may comprise features for mating with the pivoting arms of the tensioner tool 430. For example, the superior surface of the upper platform 405B may comprise one or more keying features configured to mate with a lower arm of the tensioner tool 430. For example, the keying feature may be a groove that is complementary to a shape of a portion of the lower arm. Accordingly, the lower arm may be placed in contact with the keying feature to secure a position of the tensioner tool 430. The keying feature may secure the tensioner tool 430 within the cavity and reduce or prevent unwanted movement of the tensioner tool 430. For example, the keying feature may secure at least a lateral and/or anterior-posterior pose (i.e., position and/or orientation) of the tensioner tool 430, thereby preventing lateral movement and/or anterior-posterior movement of the tensioner tool 430. Accordingly, the tensioner tool 430 may be stabilized during distraction of the joint as described herein to reduce the likelihood of slipping and/or dislodging of the tensioner tool 430.

In another example, the interior surfaces of the superior spacer 410 that define the cavity 415 may comprise one or more keying features configured to mate with an upper arm of the tensioner tool 430. For example, the keying feature may be a groove that is complementary to a shape of a portion of the upper arm. In some embodiments, the upper arm of the tensioner tool 430 comprises two or more prongs, e.g., a fork shape. Accordingly, the keying feature may be a fork-shaped groove (e.g., a U-shaped groove) configured to receive the two or more prongs. The upper arm may be received by the keying feature to secure the tensioner tool 430 within the cavity and reduce or prevent unwanted movement of the tensioner tool 430. For example, the keying feature may secure at least a lateral and/or anterior-posterior pose (i.e., position and/or orientation) of the tensioner tool 430, thereby preventing lateral movement and/or anterior-posterior movement of the tensioner tool 430. Accordingly, the tensioner tool 430 may be stabilized during distraction of the joint as described herein to reduce the likelihood of slipping and/or dislodging of the tensioner tool 430. In some embodiments, the keying features may only engage the upper arm during distraction of the joint. For example, the keying features may be positioned above the inserted portion of the tensioner tool 430 when the tensioner tool 430 is in a compressed configuration. Further, when the tensioner tool 430 is expanded within the cavity 415 (e.g., by separating the arms of the tensioner tool 430), the keying features formed in the interior surfaces of the superior spacer 410 may receive and engage with the upper arm of the tensioner tool 430 to stabilize the tensioner tool 430 during distraction. In additional embodiments, the keying features may only engage the upper arm if the tensioner tool 430 in both the compressed and expanded configurations such that the tensioner tool 430 is stabilized by the keying features before, during, and after distraction of the joint.

In some embodiments, the superior spacer 410 may comprise features for engaging with a surface associated with the femur of the joint, e.g., a femoral component. For example, the superior spacer 410 may comprise one or more surface features 335 such as protrusions, grooves, depressions, and the like, which are configured to receive and mate with a surface of a femoral component contacting the superior spacer 410 (as shown in FIGS. 4A-4B). In some embodiments, the surface features 335 are formed on the superior surface of the superior spacer 410.

In use, the superior spacer 410 may be selectively moved from a first position in contact with the superior surface of the upper platform 405B to a second position separated from the superior surface of the upper platform 405B. For example, as further described herein, the tensioner tool 430 may be used to apply a force between the superior spacer 410 and the upper platform 405B by spreading the upper arm and lower arm. Accordingly, the superior spacer 410 may be lifted away from the upper platform 405B to distract the joint.

In some embodiments, the superior spacer 410 performs translational movement between the first position and the second position. For example, the superior spacer 410 may translate along a longitudinal axis of the base plate 405.

In some embodiments, the superior spacer 410 pivots with respect to the base plate 405 between the first position and the second position. For example, the superior spacer 410 may pivot in a similar manner as the pivoting motion of the upper and lower arms of the tensioner tool 430 during distraction.

Movement of the superior spacer 410 may be constrained in one or more degrees of freedom in order to prevent unwanted movement, e.g., by a coupling to the upper platform 405B. In some embodiments, the superior spacer 410 may move with respect to a single translational axis (e.g., the longitudinal axis of the base plate 405) and may be locked in the two translational axes orthogonal thereto. In some embodiments, the superior spacer 410 may pivot with respect to a single rotational axis and may be locked in the two rotational axes orthogonal thereto. In some embodiments, the superior spacer 410 may be locked with respect to one, two, or three rotational axes of movement.

In some embodiments, the superior spacer 410 is formed from a polymer. However, it should be understood that various materials may be used to form the superior spacer 410 as would be understood by a person having an ordinary level of skill in the art. The selected material may be suitable for contacting the femoral component safely and effectively under a force and/or for interfacing with the tensioner tool 430.

The devices, systems, and methods as described herein are not intended to be limited in terms of the particular embodiments described, which are intended only as illustrations of various features. Many modifications and variations to the devices, systems, and methods can be made without departing from their spirit and scope, as will be apparent to those skilled in the art.

As described, the one or more cavities 415 may be configured to align with medial and/or lateral compartments of the joint to distract each portion of the joint individually. In some embodiments, the superior spacer 410 may be separable into multiple portions and/or comprise multiple separate pieces, wherein each portion or piece comprises a cavity 415. In some embodiments, the superior spacer 410 may comprise multiple regions movable with respect to one another, wherein each region comprises a cavity 415. For example, superior spacer 410 may comprise a medial cavity 415 comprising the medial cavity and a lateral portion comprising the lateral cavity 415. The medial and lateral portions may be removably coupled and/or may be configured to rotationally and/or translationally move with respect to one another. Accordingly, when one of the medial and lateral compartments are distracted, the portions or pieces of the superior spacer 410 may move independently.

In some embodiments, in addition or as an alternative to medial and/or lateral cavities as shown and described, the superior spacer may comprise a central cavity 415 substantially aligned with the anterior-posterior (AP) axis of the joint. Accordingly, the tensioner tool 430 may be inserted in the central cavity 415 and force may be applied to distract the joint from a central position along the AP axis, thereby tensioning both condyles of the femur and/or the corresponding compartments simultaneously.

Figure 6A:
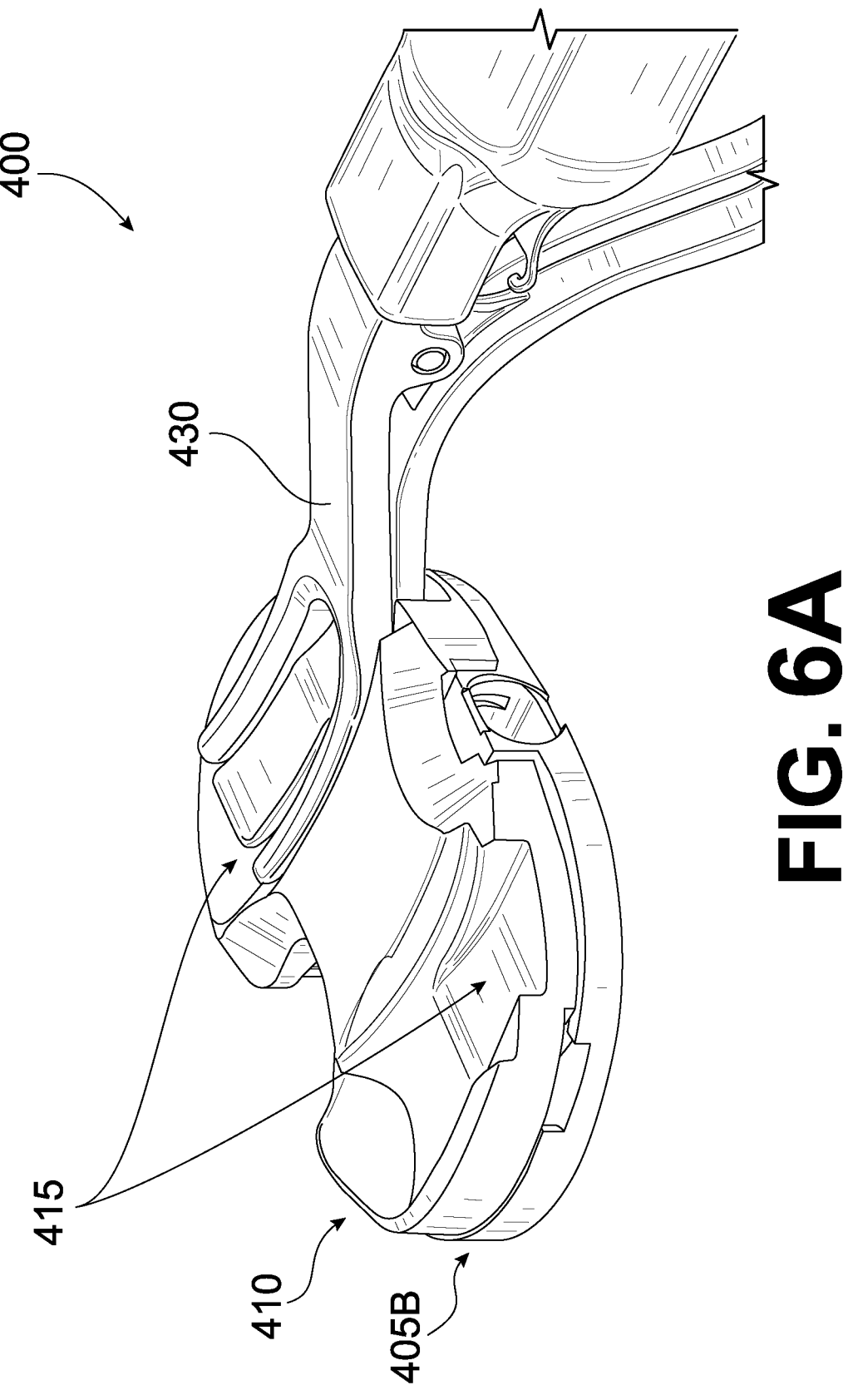
FIGS. 6A-6C depict an alternate embodiment of device for assessing laxity of a joint in accordance with an embodiment.
Figure 6B:
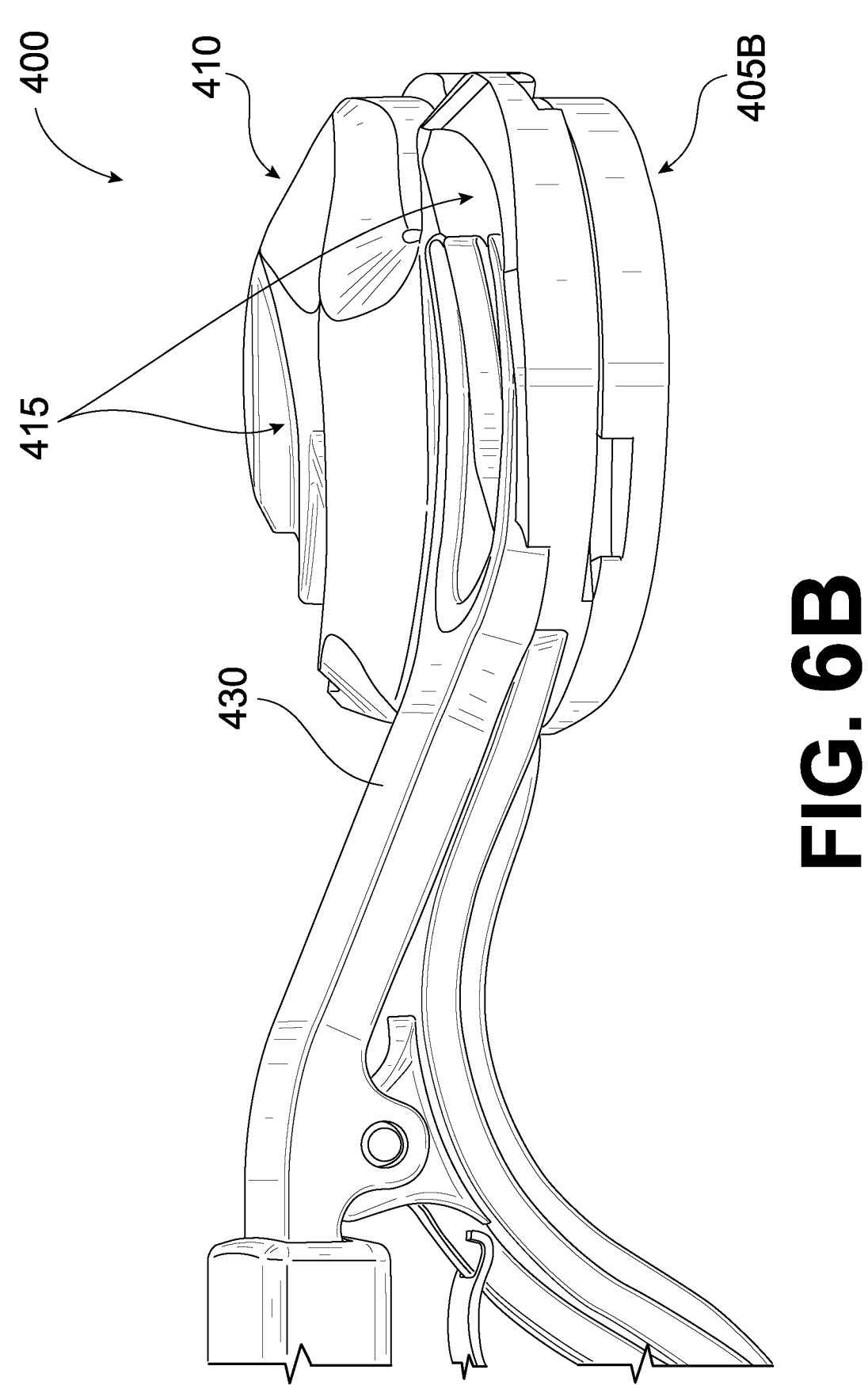
Figure 6C:
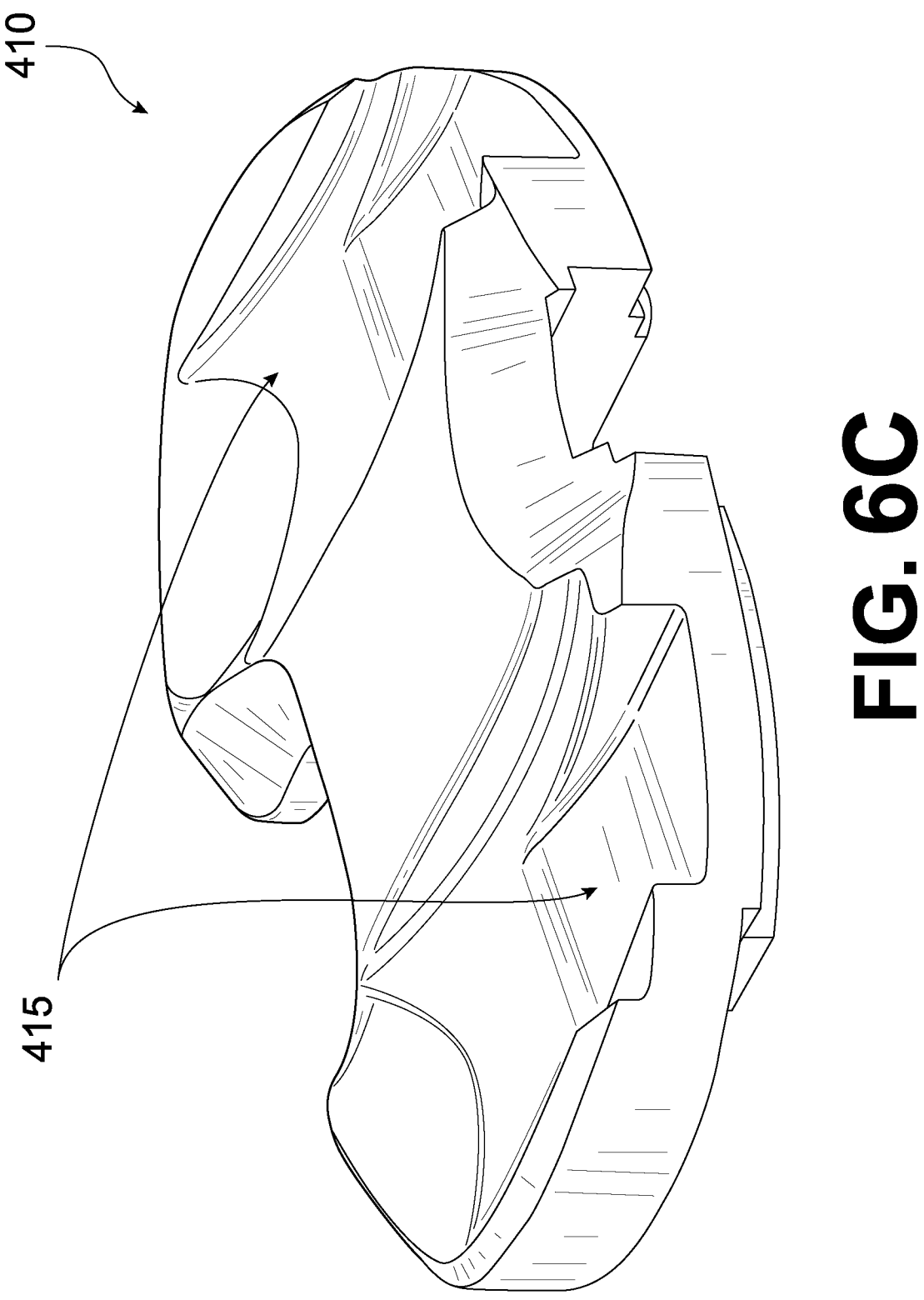

While the cavities 415 are described and depicted as being defined between the upper platform 405B and the superior spacer 410, it should be understood that various configurations of the cavities 415 are possible. Referring now to FIGS. 6A-6C, an alternate embodiment of device 400 for assessing laxity of a joint is depicted in accordance with an embodiment. As shown, the cavities 415 may be formed on a superior surface of the superior spacer 410. For example, the cavities 415 may have a depth substantially equal to a thickness of the insertion portion 415 of the tensioner tool 430 in its compressed configuration. Accordingly, insertion geometry of the tensioner tool into the cavity 415 may have zero-thickness, wherein the femoral and tibial components are not disturbed from their natural positions. In this embodiment, the tensioner tool 430 may contact the superior spacer 410 at its lower arm and the femoral component at its upper arm to apply a force therebetween to distract the joint. In such embodiments, tensioning occurs from a location corresponding to a space between a tibia and a femur in the manner similar to conventional joint tensioning without requiring a minimum thickness of insertion as typically associated with conventional tensioning. FIG. 6C depicts an isolated view of the superior spacer 410 of the device 400 of FIGS. 6A-6B. In some embodiments, the superior spacer 410 may not be configured to move with respect to the upper platform 405B and/or may not be required to move with respect to the upper platform 405B, because distraction occurs between the superior spacer 410 and the femoral component as described. Accordingly, the upper platform 405B and the superior spacer 410 may be replaced by a single unitary component forming the upper platform 405B of the base plate 405. For example, the superior spacer 410 as shown in FIG. 6C may comprise a single unitary component that replaces the upper platform 405B and the superior spacer 410 as shown in FIGS. 6A-6B.

System for Assessing Laxity of Joint

Figure 7:
FIG. 7 depicts a block diagram of an illustrative system for assessing laxity of a joint in accordance with an embodiment.
Figure 7:
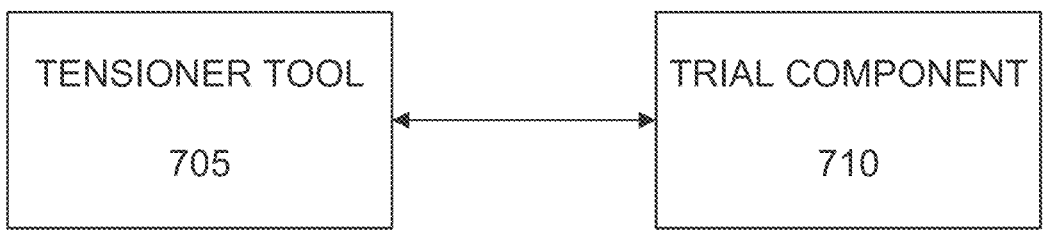
Figure 7:
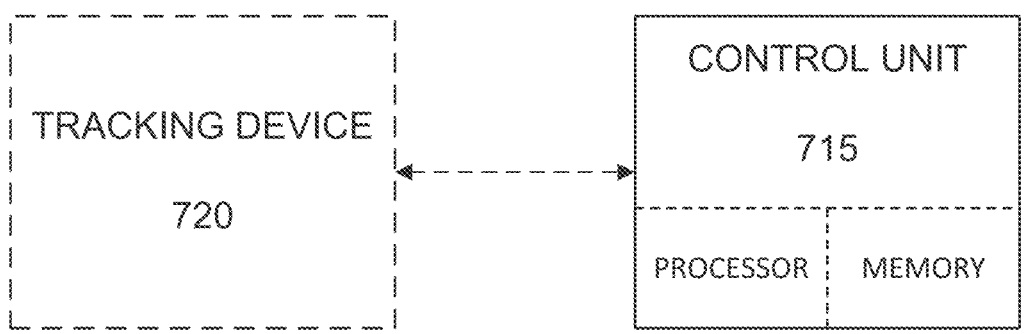

Turning now to FIG. 7, a block diagram of an illustrative system for assessing laxity of a joint is depicted in accordance with an embodiment. The system 700 comprises a tensioner tool 705, a trial component 710, and a control unit

715 including a processor and a memory. In some embodiments, the system 700 may further comprise a tracking device 720.

The tensioner tool 705 may comprise a pair of pivoting arms, i.e., an upper arm and a lower arm. The pivoting arms may be configured to pivot about a pivot axis between a compressed configuration where the upper arm and the lower arm contact one another, and an expanded configuration where the upper arm and the lower arm are separated. The distal ends of the pivoting arms may further define an insertion portion configured to be inserted within a joint and/or within a trial component 710 as further described herein. It should be understood that the tensioner tool 705 may be a tensioner tool similar to the tensioner tool 430 as described herein with respect to FIGS. 4-6 and may include any of the features and/or functions as described with respect to the tensioner tool 430.

The trial component 710 may comprise a base plate, superior spacer, and one or more cavities defined between the base plate and the superior spacer. In some embodiments, the superior spacer is in contact with the base plate in a first position and spaced from the base plate in a second position. It should be understood that the trial component 710 may be a device 400 as described herein with respect to FIGS. 4-6 and may include any of the features and/or functions as described with respect to the device 400.

The control unit 715 may be in electrical communication with the tracking device 720 to receive location information therefrom. In some embodiments, the control unit 715 includes a processor and a memory such as a non-transitory, computer-readable medium storing instructions for receiving location information and/or determining a gap distance associated with the joint based on the location information. It should be understood that the control unit 715 may be a surgical computer 150 as described herein with respect to the CASS 100 of FIG. 1 and may include any number of components, features, and/or functions as described herein with respect to the surgical computer 150.

The tracking device 720 may comprise one or more sensors configured to detect a position of at least a portion of the trial component 710, e.g., a superior spacer thereof. In some embodiments, the tracking device 720 comprises optical sensors, e.g., IR sensors for detecting one or more IR markers associated with the trial component 710. In some embodiments, the tracking device 720 comprises a camera for optical detection of a position of at least a portion of the trial component 710. It should be understood that the tracking device 720 may be a tracking system 115 as described herein with respect to the CASS 100 of FIG. 1 and may include any number of components, features, and/or functions as described herein with respect to the tracking system 115.

Figure 8:
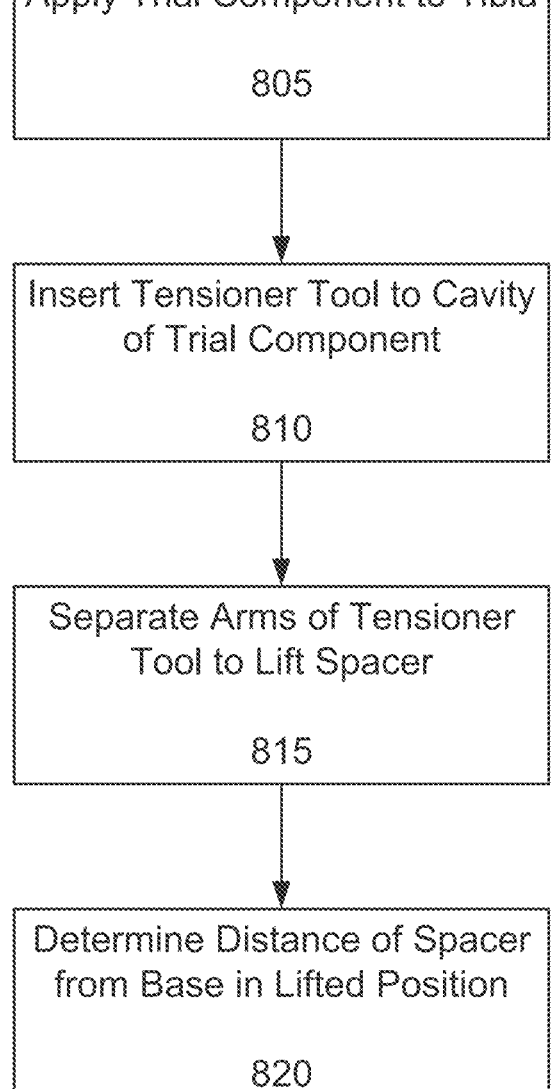
FIG. 8 depicts a flow diagram of an illustrative method for assessing laxity of a joint using the system in accordance with an embodiment.

Turning now to FIG. 8, a flow diagram of an illustrative method 800 for assessing laxity of a joint using the system 700 is depicted in accordance with an embodiment. For example, the method 700 may be carried out by a surgeon using the tensioner tool 705 and the trial component 710, with certain steps performed by the processor of the control unit 715 upon execution of the instructions stored on the memory. The method 800 comprises applying 805 the trial component 710 to a tibia of the joint, inserting 810 the tensioner tool 705 within the cavity of the trial component 710, separating 815 the arms of the tensioner tool 705 to move the superior spacer of the trial component 710 from a first position to a second position, and determining 820 a first distance associated with the second position of the superior spacer of the trial component 710.

In some embodiments, the base plate of the trial component 710 may be applied 805 to the tibia such that an upper platform of the trial component 710 extends away from the tibia. In some embodiments, the upper platform defines a superior surface that faces a second bone of the joint, e.g., a femur. As further described, the superior surface may be configured to receive the superior spacer thereon.

In some embodiments, the cavity of the trial component 710 may receive the insertion portion of the tensioner tool 705. In some embodiments, the cavity comprises a geometry configured to mate with the tensioner tool 705. For example, the surfaces of the base plate and/or the superior spacer that define the cavity may comprise features for mating with the pivoting arms of the tensioner tool 705. For example, the surfaces comprise one or more keying features configured to mate with one or more of the pivoting arms of the tensioner tool 705 to secure a position thereof within the cavity. The keying features may reduce or prevent unwanted movement of the tensioner tool 705, e.g., lateral movement and/or anterior-posterior movement of the tensioner tool 705, thereby stabilizing the tensioner tool 705 during distraction of the joint as described herein to reduce the likelihood of slipping and/or dislodging of the tensioner tool 705.

In some embodiments, the superior spacer of the trial component is moved from a first position in contact with the base plate to a second position separated from the base plate (e.g., a superior surface thereof). In some embodiments, separating 815 the arms of the tensioner tool 705 applies a force between the superior spacer and the base plate, thereby lifting the superior spacer away from the base plate to distract the joint.

In some embodiments, the tracking device 720 may detect a location of the first bone and the second bone when the superior spacer is in the second position. For example, the tracking device 720 may detect one or more optical markers on the first bone and the second bone (or surfaces corresponding thereto) to detect locations of the first bone and the second bone. Accordingly, the processor of the control unit 715 may receive the location information and determine a gap distance between the first bone and the second bone based on the location information. In such embodiments, the first distance associated with the second position of the superior spacer determined 820 by the control unit 715 may be a gap distance between the first bone and the second bone. For example, the processor of the control unit 715 may receive the location information associated with the first bone and the second bone as described above and determine a gap distance between the first bone and the second bone based on the location information. In some embodiments, the first distance is determined 820 based further on baseline locations of the first bone and the second bone collected prior to distraction.

In some embodiments, the tracking device 720 may detect a location of the superior spacer and/or the base plate in the second position. For example, the tracking device 720 may detect one or more optical markers on the superior spacer and/or the base plate to detect locations of the superior spacer and/or the base plate. Accordingly, the processor of the control unit 715 may receive the location information and determine a first distance between the base plate and the superior spacer in the second position based on the location information. In some embodiments, the first distance associated with the second position of the superior spacer determined 820 by the control unit 715 may be used to further determine a gap distance between the first bone and the second bone. For example, the processor of the control unit 715 may determine, based on the first distance, a gap distance between the first bone and the second bone. In some embodiments, the gap distance is equal to the first distance. In some embodiments, the gap distance is different from the first distance and may be determined further on baseline locations of the first bone and the second bone collected prior to distraction.

In some embodiments, the tracking device 720 may capture one or more images of the superior spacer and/or the base plate in the second position. For example, the tracking device 720 may comprise a camera that captures an image of the superior spacer and/or the base plate. Accordingly, the processor of the control unit 715 may receive the one or more images and process the images to determine the first distance between the base plate and the superior spacer in the second position based on the location information.

In some embodiments, a tracking device 720 may not be utilized. For example, the tensioner tool 705 may be in electrical communication with the control unit 715 and may comprise sensors to detect a distance between the pivoting arms of the tensioner tool 705 in the second position. Accordingly, the processor of the control unit 715 may receive information from the sensors of the tensioner tool 705 related to the distance between the arms. The control unit 715 may determine the first distance between the base plate and the superior spacer in the second position based on the received information and/or the distance between the pivoting arms.

In additional embodiments, the first distance between the superior spacer and the base plate in the second position may be manually measured or read by a medical professional and may be inputted to the control unit 715 via an input device.

In some embodiments, the first distance between the superior spacer and the base plate in the second position is equal to an associated gap distance between the first bone and the second bone. However, in some embodiments, the gap distance may vary from the first distance due to various biomechanical interactions. For example, distracting the joint from an offset position (i.e., not at the natural interface of the tibia and the femur or corresponding components) as compared to conventional joint tensioning methods may have biomechanical effects that impact the distance of distraction. Accordingly, the gap distance associated with the first bone and the second bone may be determined by the processor based on a known relationship between the first distance and the gap distance. For example, the gap distance may be calculated based on known dimensions and geometries of the tensioner tool 705, the trial component 710, and the joint of the patient, as well as the applied force.

In some embodiments, the method 800 may be repeated multiple times. In some embodiments, the method 800 is performed for each of the medial and/or lateral compartments of the joint by using an associated cavity of the trial component 715. Accordingly, a second distance may be determined in a similar manner as the first distance. In some embodiments, the method 800 is performed for each of a plurality of poses of the joint through a range of motion. In some embodiments, the joint is moved through a range of motion during the separating 815 process. Accordingly, a plurality of second distances may be determined in the same manner as the first distance. The first distance and the second distance(s) may be compared and/or charted together, which may provide insights related to the biomechanical interactions of the joint as well as the stability of the joint with the inserted trial components.

The devices, systems, and methods as described herein are not intended to be limited in terms of the particular embodiments described, which are intended only as illustrations of various features. Many modifications and variations to the devices, systems, and methods can be made without departing from their spirit and scope, as will be apparent to those skilled in the art.

While the systems and methods described herein refer to collection of force measurements by a force sensor on the tensioner tool, it should be understood that force measurements may be collected in a variety of manner. In an alternative embodiment, the trial component 710 may comprise force sensors on a portion thereof. For example, force sensors may be embedded in and/or disposed on the superior spacer, the base plate, and/or other surfaces against which the tensioning force would be exerted. In another example, force sensors may be embedded in and/or disposed on a removable liner applied to the trial component 710 and/or the tensioner tool 705. The force sensors may communicate with the control unit 715 to communicate sensed forces, thereby enabling determination of the applied force by the tensioner tool 705. In such embodiments, the tensioner tool may not comprise force sensors.

In some embodiments, the system 700 collects, records, and/or determines a plurality of distances (e.g., the first distance and/or the gap distance) for the joint. In some embodiments, each distance is collected, recorded, and/or determine for each of a plurality of poses of the joint along a range of motion. In some embodiments, each distance is collected, recorded, and/or determine for each of a plurality of locations of the joint surface, e.g., medial compartment, lateral compartment, at the AP axis, and the like. However, in additional embodiments, the system may select a maximum first distance and/or gap distance for use in further calculations. For example, a surgeon may be particularly concerned with a maximum gap in the post-operative joint under the applied force. Accordingly, while a plurality of distances may be collected, the system 700 may utilize the greatest first distance and/or gap distance from amongst the plurality of distances for recording, display, and/or additional calculation.

Data Processing Systems for Implementing Embodiments Herein

Figure 9:
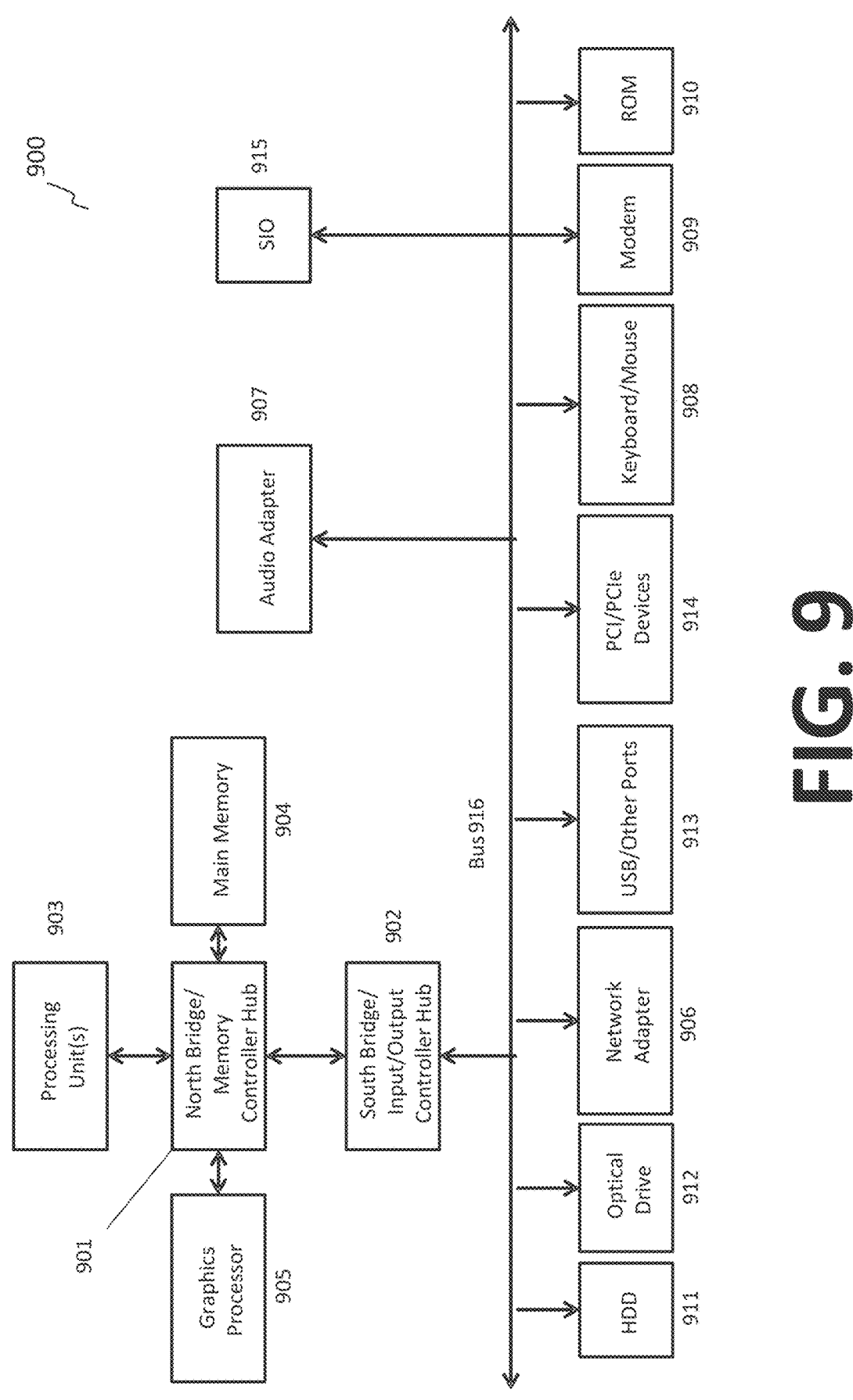
FIG. 9 illustrates a block diagram of an exemplary data processing system in which embodiments are implemented.
Figure 10:
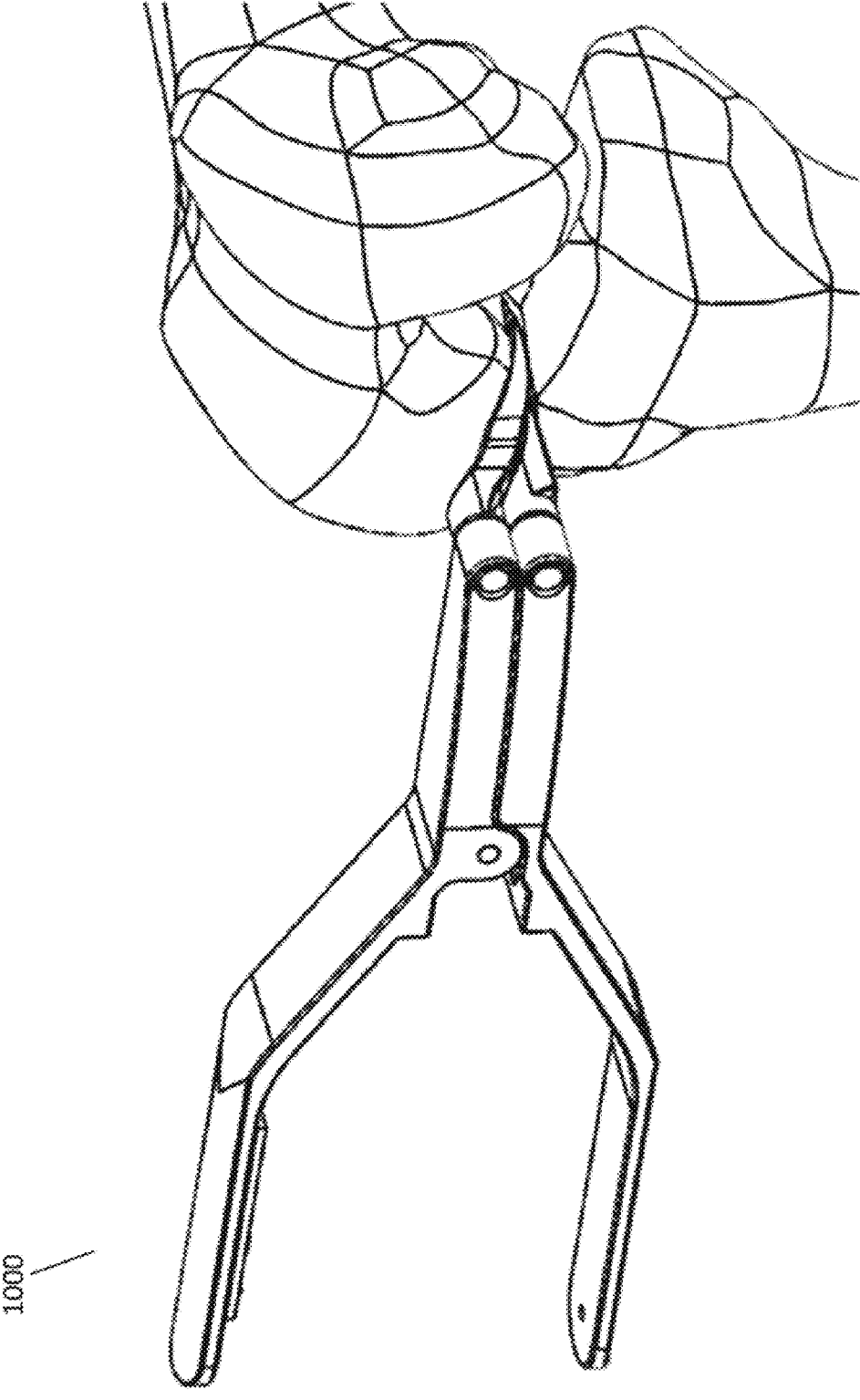
FIG. 10 depicts a prior art tensioner tool inserted in a knee joint in accordance with an embodiment.

FIG. 9 illustrates a block diagram of an exemplary data processing system 900 in which embodiments are implemented. The data processing system 900 is an example of a computer, such as a server or client, in which computer usable code or instructions implementing the process for illustrative embodiments of the present invention are located. In some embodiments, the data processing system 900 may be a server computing device. For example, data processing system 900 can be implemented in a server or another similar computing device operably connected to a surgical system 100 and/or a system 700 as described above. The data processing system 900 can be configured to, for example, transmit and receive information related to a patient and/or a related surgical plan with the surgical system 100 and/or system 700.

In the depicted example, data processing system 900 can employ a hub architecture including a north bridge and memory controller hub (NB/MCH) 901 and south bridge and input/output (I/O) controller hub (SB/ICH) 902. Processing unit 903, main memory 904, and graphics processor 905 can be connected to the NB/MCH 901. Graphics processor 905 can be connected to the NB/MCH 901 through, for example, an accelerated graphics port (AGP).

In the depicted example, a network adapter 906 connects to the SB/ICH 902. An audio adapter 907, keyboard and mouse adapter 908, modem 909, read only memory (ROM) 910, hard disk drive (HDD) 911, optical drive (e.g., CD or DVD) 912, universal serial bus (USB) ports and other communication ports 913, and PCI/PCIe devices 914 may connect to the SB/ICH 902 through bus system 916. PCI/PCIe devices 914 may include Ethernet adapters, add-in cards, and PC cards for notebook computers. ROM 910 may be, for example, a flash basic input/output system (BIOS). The HDD 911 and optical drive 912 can use an integrated drive electronics (IDE) or serial advanced technology attachment (SATA) interface. A super I/O (SIO) device 915 can be connected to the SB/ICH 902.

An operating system can run on the processing unit 903. The operating system can coordinate and provide control of various components within the data processing system 900. As a client, the operating system can be a commercially available operating system. An object-oriented programming system, such as the Java™ programming system, may run in conjunction with the operating system and provide calls to the operating system from the object-oriented programs or applications executing on the data processing system 900. As a server, the data processing system 900 can be an IBMR eServer™ System® running the Advanced Interactive Executive operating system or the Linux operating system. The data processing system 900 can be a symmetric multiprocessor (SMP) system that can include a plurality of processors in the processing unit 903. Alternatively, a single processor system may be employed.

Instructions for the operating system, the object-oriented programming system, and applications or programs are located on storage devices, such as the HDD 911, and are loaded into the main memory 904 for execution by the processing unit 903. The processes for embodiments described herein can be performed by the processing unit 903 using computer usable program code, which can be located in a memory such as, for example, main memory 904, ROM 910, or in one or more peripheral devices.

A bus system 916 can be comprised of one or more busses. The bus system 916 can be implemented using any type of communication fabric or architecture that can provide for a transfer of data between different components or devices attached to the fabric or architecture. A communication unit such as the modem 909 or the network adapter 906 can include one or more devices that can be used to transmit and receive data.

Those of ordinary skill in the art will appreciate that the hardware depicted in FIG. 9 may vary depending on the implementation. Other internal hardware or peripheral devices, such as flash memory, equivalent non-volatile memory, or optical disk drives may be used in addition to or in place of the hardware depicted. Moreover, the data processing system 900 can take the form of any of a number of different data processing systems, including but not limited to, client computing devices, server computing devices, tablet computers, laptop computers, telephone or other communication devices, personal digital assistants, and the like. Essentially, data processing system 900 can be any known or later developed data processing system without architectural limitation.

While various illustrative embodiments incorporating the principles of the present teachings have been disclosed, the present teachings are not limited to the disclosed embodiments. Instead, this application is intended to cover any variations, uses, or adaptations of the present teachings and use its general principles. Further, this application is intended to cover such departures from the present disclosure as come within known or customary practice in the art to which these teachings pertain.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. It is also to be understood that the terminology used herein is for the purpose of describing particular embodiments only and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices also can "consist essentially of" or "consist of" the various components and steps, and such terminology should be interpreted as defining essentially closed-member groups.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by $\frac{1}{10}$ of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the present disclosure include equivalents to the recited values, e.g., variations in the numerical quantity of such values that can occur, but would be recognized to be equivalents by a person skilled in the art.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A device for assessing laxity in a joint, the device comprising:

a trial component configured to be coupled to a first bone of the joint, the trial component comprising a base plate configured to couple to the first bone and a superior spacer coupled to the base plate, wherein the base plate and the superior spacer define a cavity therebetween, the cavity configured to receive a portion of a tensioner tool, wherein the superior spacer is configured to be selectively moved between a first position in contact with a superior surface of the base plate and a second position separated from the superior surface.

2. The device of claim 1, wherein the superior surface comprises a keying feature configured to mate with a surface feature on the portion of the tensioner tool, thereby securing an anterior-posterior pose of the tensioner tool.

3. The device of claim 1, wherein a cross-sectional geometry of the superior surface substantially matches a cross-sectional geometry of the superior spacer.

4. The device of claim 1, wherein the superior spacer pivots with respect to the superior surface of the base plate as the superior spacer moves between the first position and the second position.

5. The device of claim 1, wherein the superior spacer translates along a longitudinal axis of the base plate as the superior spacer moves between the first position and the second position.

6. The device of claim 5, wherein translation of the superior spacer is locked with respect to a first axis and a second axis, wherein the first axis is orthogonal to the second axis, wherein each of the first axis and the second axis is orthogonal to the longitudinal axis.

7. The device of claim 1, wherein the superior spacer is formed from a polymer.

8. The device of claim 1, wherein the joint is a knee joint and the first bone is a tibia.

9. The device of claim 1, wherein the joint is a shoulder joint.

10. A system for assessing laxity in a joint having a first bone and a second bone, the system comprising:

a tensioner tool comprising a pair of arms defining an insertion portion, wherein the pair of arms are configured to pivot about a pivot axis between a compressed configuration and an expanded configuration;

a trial component comprising:

a base plate configured to couple to the first bone, and a superior spacer coupled to the base plate, wherein the superior spacer is configured to be selectively moved between a first position in contact with a superior surface of the base plate and a second position separated from the superior surface, wherein the base plate and the superior spacer define a cavity therebetween, the cavity configured to receive the insertion portion of the tensioner tool therein;

a processor; and a non-transitory, computer-readable medium storing instructions that, when executed, cause the processor to:

receive information related to a distance between the superior surface of the base plate and the superior spacer in the second position, and determine, based on the information, a gap distance associated with the first bone and the second bone.

11. The system of claim 10, wherein the cavity is configured to receive the insertion portion of the tensioner tool in the compressed configuration.

12. The system of claim 10, wherein the superior spacer is configured to move from the first position to the second position when the tensioner tool pivots from the compressed configuration to the expanded configuration within the cavity.

13. The system of claim 10, wherein the superior surface comprises a first keying feature and the tensioner tool comprises a second keying feature complementary to the first keying feature, wherein the first keying feature is configured to mate with the second keying feature when the insertion portion is received within the cavity.

14. The system of claim 10, wherein the first keying feature, when mated with the second keying feature, secures an anterior-posterior pose of the tensioner tool.

15. The system of claim 10, wherein a cross-sectional geometry of the superior surface substantially matches a cross-sectional geometry of the superior spacer.

16. The system of claim 10, wherein the superior spacer pivots with respect to the superior surface of the base plate as the superior spacer moves between the first position and the second position.

17. The system of claim 10, wherein the superior spacer translates along a longitudinal axis of the base plate as the superior spacer moves between the first position and the second position.

18. The system of claim 17, wherein translation of the superior spacer is locked with respect to a first axis and a second axis, wherein the first axis is orthogonal to the second axis, wherein each of the first axis and the second axis is orthogonal to the longitudinal axis.

19. The system of claim 10, wherein the superior spacer is formed from a polymer.

20. The system of claim 10, wherein the joint is a knee joint, the first bone is a tibia, and the second bone is a femur.

21. The system of claim 10, wherein the joint is a shoulder joint.

22. A method of assessing laxity in a joint, the method comprising:

applying a trial component to a first bone of the joint, the trial component comprising a base plate configured to couple to the first bone and a superior spacer coupled to the base plate;

inserting an insertion portion of a tensioner tool within a cavity defined between the base plate and the superior spacer, the insertion portion comprising a pair of arms;

separating the pair of arms, thereby causing the superior spacer to move from a first position in contact with a superior surface of the base plate to a second position spaced from the superior surface; and determining a first distance between the superior surface of the base plate and the superior spacer in the second position.

* * * * *